US008987304B2

(12) United States Patent
Matsumoto et al.

(10) Patent No.: US 8,987,304 B2
(45) Date of Patent: Mar. 24, 2015

(54) ANTITUBERCULOUS COMPOSITION COMPRISING OXAZOLE COMPOUNDS

(75) Inventors: Makoto Matsumoto, Tokushima (JP);
Hiroyuki Hashizume, Tokushima (JP);
Tatsuo Tomishige, Tokushima (JP);
Masanori Kawasaki, Tokushima (JP);
Yoshihiko Shimokawa, Tokushima (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 1072 days.

(21) Appl. No.: 12/088,867

(22) PCT Filed: Oct. 4, 2006

(86) PCT No.: PCT/JP2006/320239
§ 371 (c)(1),
(2), (4) Date: Apr. 1, 2008

(87) PCT Pub. No.: WO2007/043542
PCT Pub. Date: Apr. 19, 2007

(65) Prior Publication Data
US 2009/0275528 A1   Nov. 5, 2009

(30) Foreign Application Priority Data
Oct. 5, 2005 (JP) ................................ 2005-292461

(51) Int. Cl.
*A61K 31/454* (2006.01)
*A61K 31/496* (2006.01)
(Continued)

(52) U.S. Cl.
CPC ............. *A61K 31/451* (2013.01); *A61K 31/424* (2013.01); *A61K 31/454* (2013.01); *A61K 31/496* (2013.01); *A61K 45/06* (2013.01)
USPC ...... 514/322; 514/254.11; 514/354; 514/669; 514/42; 514/252.1

(58) Field of Classification Search
USPC .............. 514/326, 322, 254.11, 354, 669, 42, 514/252.1
See application file for complete search history.

(56) References Cited

U.S. PATENT DOCUMENTS
2006/0094767 A1   5/2006   Tsubouchi et al.

FOREIGN PATENT DOCUMENTS
DE   3911263 A1   10/1990
EP   1 555 267 A1   7/2005
(Continued)

OTHER PUBLICATIONS
The American Thoracic Society "American Thoracic Society/Center for Disease Control and pPrevention/infectious Diseases Society of America: Treatment of Tuberculosis," Am. J. Respir. Crit. Care Med. 2003, vol. 167, pp. 603-662.*
(Continued)

*Primary Examiner* — Shengjun Wang
(74) *Attorney, Agent, or Firm* — Finnegan, Henderson, Farabow, Garrett & Dunner, L.L.P.

(57) ABSTRACT

The present invention provides antituberculous therapeutic drugs with a higher potency. The present invention provides also antituberculous therapeutic drugs containing oxazole compounds represented by (I) general formula (1): [wherein $R^1$ represents a hydrogen atom or C1-6 alkyl group, n represents an integer of 0-6, and $R^2$ represents general formula (A) or the like, wherein $R^3$ represents a phenoxy group (at least one group selected from the group consisting of a halogen atom, an optionally halogen-substituted C1-6 alkyl group and an optionally halogen-substituted C1-6 alkoxy group may be substituted on the phenyl ring) or the like], optically active forms thereof or salts thereof, and drugs (II) such as primary antituberculous drugs.

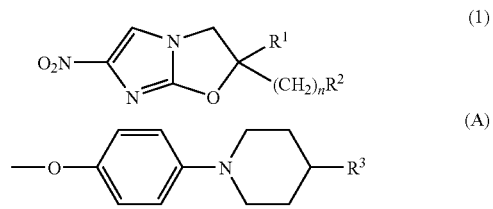

3 Claims, 2 Drawing Sheets

(51) Int. Cl.
*A61K 31/4409* (2006.01)
*A61K 31/133* (2006.01)
*A61K 31/70* (2006.01)
*A61K 31/50* (2006.01)
*A61K 31/451* (2006.01)
*A61K 31/424* (2006.01)
*A61K 45/06* (2006.01)

(56) References Cited

FOREIGN PATENT DOCUMENTS

| RU | 2121838 C1 | | 11/1998 |
|---|---|---|---|
| WO | WO 2004/033463 | * | 4/2004 |
| WO | WO 2005/042542 A | | 5/2005 |
| WO | WO 2005/092832 A1 | | 10/2005 |

OTHER PUBLICATIONS

Office Action dated May 19, 2010 issued in corresponding Belarus patent application.

G. A. Melentieva et al., Pharmaceutical Chemistry, Moscow Medicina, 1993, pp. 6-9.

B. Dautzenberg et al., "Traitement des mycobactérioses à mycobactéries non tuberculeuses", Med. Mal. Infact. 1991; 21, 115-120.

Office Action dated Jul. 21, 2010 corresponding Russian Application No. 2008117427.

Michael D. Iseman, "A Clinician's Guide to Tuberculosis," by Lippincott Williams & Wilkins, USA, ISBN 0-7817-1749-3; pp. 276-295 (2000).

Kuse et al., Kekkaku $2^{nd}$ Edition (1992).

Katsuhiro Suzuki et al., Kekkaku vol. 74: 77-82 (1999).

"Scientific Blueprint for Tuberculosis Drug Development," 2001 The Global Alliance for TB Drug Development, Inc., pp. 1-52 (2001).

Earl Hershfield, "Tuberculosis: 9. Treatment," CMAJ; 161 (4): pp. 405-411, 1999.

F. A. Drobniewski et al., "Tuberculosis and AIDS," J. Med. Microbiol. 1995; 43, pp. 85-91.

W. W. Yew et al., "Drug-Resistant tuberculosis in the 1990s," Eur. Respir. J. 1'995, 8; pp. 1184-1192.

* cited by examiner

VIABLE CELL COUNTS IN THE LUNG AFTER
8 WEEKS TREATMENT

ANTITUBERCULOUS COMPOSITION COMPRISING OXAZOLE COMPOUNDS

TECHNICAL FIELD

The present invention relates to a pharmaceutical composition.

BACKGROUND ART

It is known that 2,3-dihydro-6-nitroimidazo[2,1-b]oxazole compounds represented by the following general formula (1), optically active forms thereof and pharmacologically acceptable salts thereof (hereinafter they are simply referred to as oxazole compounds (I)) have an excellent bactericidal effect against acid-fast bacteria (*Mycobacterium tuberculosis*, multidrug-resistant *Mycobacterium tuberculosis* and atypical acid-fast bacteria) (JP-A-2004-149527 and WO2005-042542).

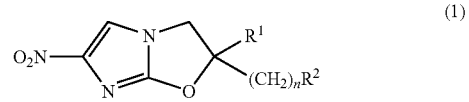
(1)

wherein $R^1$ represents a hydrogen atom or C1-6 alkyl-group. n represents an integer of 0-6. $R^2$ represents any group of the following general formulas (A)-(G).
The group represented by the general formula (A) is:

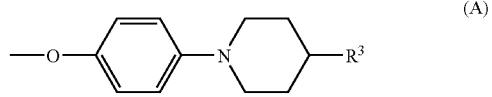
(A)

wherein $R^3$ represents any group of the following (1)-(6).
(1) a phenoxy group (at least one group selected from the group consisting of a halogen atom, an optionally halogen-substituted C1-6 alkyl group and an optionally halogen-substituted C1-6 alkoxy group may be substituted on the phenyl ring);
(2) a phenyl C1-6 alkoxy group (at least one group selected from the group consisting of a halogen atom, an optionally halogen-substituted C1-6 alkyl group and an optionally halogen-substituted C1-6 alkoxy group may be substituted on the phenyl ring);
(3) a —$NR^4R^5$ group, wherein $R^4$ represents a hydrogen atom or C1-6 alkyl group and $R^5$ represents phenyl group (at least one group selected from the group consisting of a halogen atom, an optionally halogen-substituted C1-6 alkyl group and an optionally halogen-substituted C1-6- alkoxy group may be substituted on the phenyl ring);
(4) a phenyl C1-6 alkyl group (at least one group selected from the group consisting of a halogen atom, an optionally halogen-substituted C1-6 alkyl group and an optionally halogen-substituted C1-6 alkoxy group may be substituted on the phenyl rings;
(5) a phenoxy C1-6 alkyl group (at least one group selected from the group consisting of a halogen atom, an optionally halogen-substituted C1-6 alkyl group and an optionally halogen-substituted C1-6 alkoxy group may be substituted on the phenyl ring); and
(6) a benzofuryl C1-6 alkyl group (at least one group selected from the group consisting of a halogen atom, an optionally halogen-substituted C1-6 alkyl group and an optionally halogen-substituted C1-6 alkoxy group may be substituted on the benzofuran ring);
the group represented by the general formula (B) is:

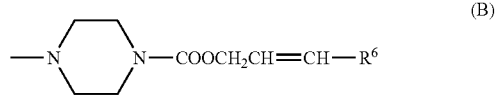
(B)

wherein $R^6$ represents phenyl group (at least one group selected from the group consisting of a halogen atom, an optionally halogen-substituted C1-6 alkyl group and an optionally halogen-substituted C1-6 alkoxy group may be substituted on the phenyl ring). The group represented by the general formula (C) is:

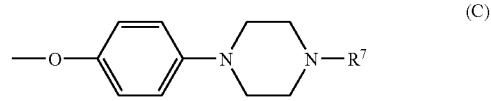
(C)

wherein $R^7$ represents a phenyl C2-10 alkenyl group (at least one group selected from the group consisting of a halogen atom, an optionally halogen-substituted C1-6 alkyl group and an optionally halogen-substituted C1-6 alkoxy group may be substituted on the phenyl ring) or a biphenyl C1-6 alkyl group (at least one group selected from the group consisting of a halogen atom, an optionally halogen-substituted C1-6 alkyl group and an optionally halogen-substituted C1-6 alkoxy group may be substituted on the phenyl ring). The group represented by the general formula (D) is:

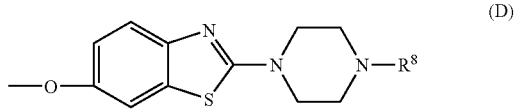
(D)

wherein $R^8$ represents a phenyl C1-6 alkyl group (at least one group selected from the group consisting of a halogen atom, an optionally halogen-substituted C1-6 alkyl group and an optionally halogen-substituted C1-6 alkoxy group may be substituted on the phenyl ring).
The group represented by the general formula (E) is:

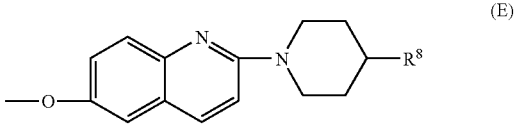
(E)

wherein $R^8$ is as described above.
The group represented by the general formula (F) is:

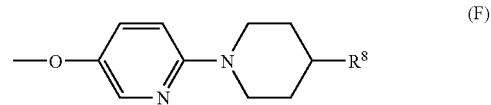
(F)

wherein $R^8$ is as described above.

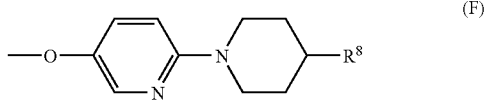

The group represented by the general formula (G) is:

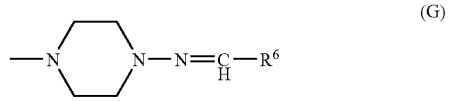

wherein $R^6$ is as described above.

Among acid-fast bacteria, human *Mycobacterium tuberculosis* is widely known and one third of human being is said to be infected. In addition, *Mycobacterium africanum, Mycobacterium bovis* and *Mycobacterium microti* are known as members, of a group of tubercle bacilli together with *Mycobacterium tuberculosis* and as mycobacteria strongly pathogenic to human beings.

To these tuberculosis, a treatment is performed using those ranked as the primary antituberculous drug, i.e. three drugs including antibacterial drug of rifamycin family (e.g. rifampicin, rifabutin, rifapentine etc.), isoniazid and ethambutol hydrochloride (or streptomycih), or four drugs including those above described plus pyrazinamide.

However, very long period of medication is required for treatment of tuberculosis, which lead to poor compliance resulting in failure of the treatment inconsiderable number of cases. For multidrug resistance of infecting *Mycobacterium tuberculosis* and tuberculosis caused by multidrug-resistant *Mycobacterium tuberculosis*, used are secondary antituberculous drugs including kanamycin, enviomycin, capreomycin, paraminosalicylic acid, cycloserine, thioacetazone; quinolone anti-bacterial drugs including ofloxacin, levofloxacin, moxifloxacin, gatifloxacin, sparfloxacin etc. due to their in vitro efficacy; and macrolide antibacterial drugs including clarithromycin and azithromycin, etc. They have, however, strong side effects and a low potency.

Further, the following side effects are reported for the primary antituberculous drugs: hepatopathy, full syndrome, drug allergy, incompatibility with other drugs due to enzymatic induction related to P450 for rifamycin and related anti-bacterial drugs; peripheral neuropathy, induction of severe hepatopathy by concomitant use of rifampicin for isoniazid; decreased vision due to optic nerve disorder for ethambutol hydrochloride; decreased hearing ability by 8th cerebral nerve disorder for streptomycin; hepatopathy, gouty attack associated with increased level of uric acid and vomiting, etc. for pyrazinamide (A Clinician's Guide To Tuberculosis, Michael D. Iseman 2000 by Lippincott Williams & Wilkins, printed in the USA, ISBN 0-7817-1749-3; Kekkaku 2nd edition (1992), by Humiyuki Kuse and Takahide Izumi, Igakushoin; Kekkabku Vol. 74: 77-82 (1999)).

There is a report in fact that cases where standard chemotherapy can not be performed owing to these side effects account for 70% of discontinued medication cases (about 23%, 52 cases) among the total cases (228 inpatient cases in total subjected to investigation) (Kekkaku Vol. 74: 77-82 (1999)).

In particular, it is known that a side effect of hepatic toxicity which is common in rifamycin and related antibacterial drug, isoniazid and pyrazinamide among five drugs used concomitantly on the first line described above develops most frequently. On the other hand, *Mycobacterium tuberculosis* which shows resistance to antituberculous drugs and that has become multidrug-resistant is increasing, making treatment more difficult.

According to the investigation by WHO (1996-1999), it is announced that among *Mycobacterium tuberculosis* isolated in the world, the ratio of those which show resistance to any of existing antituberculous drugs reaches 19%, and that of those which show multidrug-resistance is 5.1%. Carriers who are infected with these multidrug-resistant *Mycobacterium tuberculosis* has assumably reached 60 millions in the world, and further increase of multidrug-resistant *Mycobacterium tuberculosis* in the future is concerned (April 2001, as a supplement to the journal Tuberculosis, the "Scientific Blueprint for TB drug development").

Further, it is reported that the mass of death in AIDS patients is caused by tuberculosis and that the number of human beings mixed-infected with tuberculosis and HIV has reached 10.7 millions at the time point of 1997 (Global Alliance for TB drug development). In addition, it is considered that mixed infection involves a higher onset risk of tuberculosis by at least 30 times than otherwise.

Further, bacteria known to be pathogenic to human beings include *Mycobacterium avium* and *Mycobacterium intracellulare* which cause recently increasing MAC disease (Mycobacterium avium-intracellulare complex disease) and other atypical acid-fast bacteria such as *Mycobacterium kansasil, Mycobacterium marinum, Mycobacterium simiae, Mycobacterium scrofulaceum; Mycobacterium szulgai, Mycobacterium xenopi, Mycobacterium malmoense, Mycobacterium haemophilum, Mycobacterium ulcerans, Mycobacterium shimoidei, Mycobacterium fortuitum, Mycobacterium chelonae, Mycobacterium smegmatis*, and *Mycobacterium aurum*.

Currently, we are short of promising therapeutic drugs against these atypical acid-fast bacterial diseases, and in the present state, primary antituberculous drugs such as rifamycin and related anti-bacterial drugs, isoniazid, ethambutol, streptomycin and pyrazinamide, and common therapeutic drugs against microbism including quinolone antibacterial drugs or antibiotics are used in combination.

DISCLOSURE OF INVENTION

For treatment of acid-fast bacterial disease, however, longer medication is forced compared with infectious diseases caused by common bacteria, and cases of difficulty in healing and death have been reported. In order to solve such situation, development of drugs which have stronger efficacy is desired.

As a result of extensive study to solve the subject described above, the present inventors have found that the subject can be solved by using one or more drugs selected from the primary antituberculous drugs, secondary antituberculous drugs, quinolone antibacterial drugs, macrolide antibacterial drugs, sulfa drugs and anti-HIV viral drugs with a combination of at least one selected from the group consisting of oxazole compounds (I) described above. Further, a measurement of antibacterial activity of the oxazole compounds (I) against *Mycobacterium tuberculosis* showed that they expressed a strong antibacterial effect in a short time and the effect was sustained for a long period. Therefore, it has been found that clinical therapy based on intermittent administration can be practiced.

The present invention has been completed based on such findings.

The invention preferably provides antituberculous therapeutic drugs shown in items 1 to 17, drugs for treatment of tuberculosis shown in item 18 and kits for treatment of tuberculosis shown in items 24 to 30.

Item 1. An antituberculous therapeutic drug comprising:
(I) at least one selected from the group consisting of 2,3-dihydro-6-nitroimidazo[2,1-b]oxazole compounds represented by general formula (1) described above, optically active forms thereof and pharmacologically acceptable salts thereof, and
(II) at least one drug selected from the group consisting of primary antituberculous drugs, secondary antituberculous drugs, quinolone antibacterial drugs, macrolide antibacterial drugs, sulfa drugs, and anti-HIV drugs.

Item 2. The antituberculous therapeutic drug according to item 1, wherein the drug of (II) is at least one selected from the group consisting of the primary antituberculous drugs, the secondary antituberculous drugs and the quinolone antibacterial drugs.

Item 3. The antituberculous therapeutic drug according to item 2, wherein the drug selected from the primary antituberculous drug is at least one selected from the group consisting of rifamycin and related anti-bacterial drugs, isoniazid, ethambutol, streptomycin, pyrazinamide and salts thereof, and the drug selected from the secondary antituberculous drug is at least one selected from the group consisting of enviomycin, kanamycin, capreomycin, cycloserine, thioacetazone, clofazimine and salts thereof.

Item 4. The antituberculous therapeutic drug according to item 2, wherein the drug of (II) is at least one selected from the primary antituberculous drugs.

Item 5. The antituberculous therapeutic drug according to item 4, wherein the at least one selected from the primary antituberculous drugs comprises in combination (i) at least one of rifamycin and related anti-bacterial drugs and (ii) at least one selected from the group consisting of isonlazid, ethambutol, streptomycin, pyrazinamide and salts thereof.

Item 6. The antituberculous therapeutic drug according to item 5, wherein the at least one selected from the primary antituberculous drugs comprises in combination (i) at least one of rifamycin and related anti-bacterial drugs and (ii) pyrazinamide.

Item 7. The antituberculous therapeutic drug according to item 4, wherein the at least one selected from the primary antituberculous drugs comprises in combination
(i) at least one of rifamycin and related anti-bacterial drugs,
(ii) pyrazinamide, and
(iii) at least one selected from the group consisting of isoniazld, ethambutol and streptomycin.

Item 8. The antituberculous therapeutic drug according to any one of items 3 to 7, wherein the at least one of rifamycin and related anti-bacterial drugs is at least one selected from the group consisting of rifampicin, rifabutin and rifapentine.

Item 9. The antituberculous therapeutic drug according to item 8, wherein the at least one of rifamycin and related anti-bacterial drugs is rifampicin.

Item 10. The antituberculous therapeutic drug according to item 1, wherein the drug of (II) is at least one selected from the quinolone antibacterial drugs.

Item 11. The antituberculous therapeutic drug according to item 10, wherein the at least one selected from the quinolone antibacterial drugs is at least one selected from the group consisting of gatifloxacin, moxifloxacin and hydrates thereof.

Item 12. The antituberculous therapeutic drug according to item 10, wherein the at least one selected from the drugs of (II) comprises in combination at least one selected from the group consisting of gatifloxacin, moxifloxacin and hydrates thereof and at least one primary antituberculous drug.

Item 13. The antituberculous therapeutic drug according to item 12, wherein the at least one selected from the primary antituberculous therapeutic drugs comprises in combination (i) any of rifamycin and related antibacterial drugs and (ii) at least one selected from the group consisting of isoniazid, ethambutol, streptomycin, pyrazinamide and salt thereof.

Item 14. The antituberculous therapeutic drug according to item 13, wherein the at least one selected from the primary antituberculous therapeutic drugs comprises in combination (i) at least one of rifamycin and related antibacterial drugs and (ii) pyrazinamide.

Item 15. The antituberculous therapeutic drug according to item 14, wherein the at least one selected from the primary antituberculous drugs comprises in combination
(i) at least one of rifamycin and related antibacterial drugs,
(ii) pyrazinamide, and
(iii) at least one selected from the group consisting of isoniazid, ethambutol and streptomycin.

Item 16. The antituberculous therapeutic drug according to any one of items 13 to 15, wherein the at least one of rifamycin and related antibacterial drugs is at least one selected from the group consisting of rifamycin, rifabutin and rifapentine.

Item 17. The antituberculous therapeutic drug according to item 16, wherein the at least one of rifamycin and related antibacterial drugs is rifampicin.

Item 18. The antituberculous therapeutic drug according to item 1, wherein the drugs of (II) is at least one selected from the macrolide antibacterial drugs.

Item 19. The antituberculous therapeutic drug according to item 18, wherein the at least one selected from the macrolide antibacterial drugs is at least one selected from the group consisting of clarithromycin, azithromycin and hydrates thereof.

Item 20. The antituberculous therapeutic drug according to item 1, wherein the drug of (II) is at least one selected from the sulfa drugs.

Item 21. The antituberculous therapeutic drug according to item 20, wherein the at least one selected from the sulfa drugs is at least one selected from the group consisting of sulfamethizole, sulfisoxazole, sulfamonomethoxine, sulfadimethoxine, sulfamethizole, salazosulfapyridine, sulfadiazine and salts thereof.

Item 22. The antituberculous therapeutic drug according to item 1, wherein the drug of (II) is at least one selected from anti-HIV drugs.

Item 23. The antituberculous therapeutic drug according to item 22, wherein the at least one selected from the anti-HIV drugs is (a) a reverse transcriptase inhibitor based on a nucleic acid, (b) a reverse transcriptase inhibitor based on a non-nucleic acid or (c) a protease inhibitor.

Item 24. A medicament for dosing at an interval of 48 hours or more, wherein the medicament comprises at least one compound as active ingredient which is selected from the group consisting of 2,3-dihydro-6-nitroimidazo[2,1-b]oxazole compounds represented by general formula (1), optically active forms thereof and pharmacologically acceptable salts thereof.

Item 25. A kit for tuberculosis treatment, wherein the kit comprises the medicament of item 24, and at least one drug (II) selected from the group consisting of primary antituberculous drugs, secondary antituberculous drugs, quinolone antibacterial drugs, macralide antibacterial drugs, sulfa drugs and anti-HIV drugs, and wherein the kit is used to dose the medicament and the drugs at an interval of 48 hours or more.

Item 26. The kit according to item 25, wherein the drug of (II) is at least one selected from the group consisting of the primary antituberculous drugs, the secondary antituberculous drugs and the quinolone antibacterial drugs.

Item 27. The kit according to item 26, wherein at least one selected from the primary antituberculous drugs is at least one selected from the group consisting of rifamycin and related anti-bacterial drugs, isoniazid, ethambutol, streptomycin, pyrazinamide and salts thereof, and the secondary antituberculous drugs are at least one selected from the group consisting of enviomycin, kanamycin, capreomycin, cycloserine, thioacetazone, clofazimine and salts thereof, and at least one selected from the quinolone antibacterial drugs is at least one selected from the group consisting of gatifloxacin, moxifloxacin and hydrate thereof.

Item 28. The kit according to item 27, wherein the drug of (II) is at least one primary antituberculous drug selected from the group consisting of rifamycin and related anti-bacterial drugs, isoniazid, ethambutol, streptomycin, pyrazinamide and salts thereof.

Item 29. The kit according to item 28, wherein the drug(s) of (II) comprises in combination at least one primary antituberculous drug selected from the groups consisting of rifamycin and related antibacterial drugs, isonlazid, ethambutol, streptomycin, pyrazinamide and salt thereof, and at least one quinolone antibacterial drug selected from the group consisting of gatifloxacin, moxifloxacin and hydrate thereof.

Item 30. The kit according to any one of items 27 to 29, wherein the at least one selected from the rifamycin and related anti-bacterial drugs is at least one selected from the group consisting of rifampicin, rifabutin and rifapentine.

BRIEF DESCRIPTION OF THE DRAWINGS

FIG. 1-2 is a graph representing the results of in vivo experiment for combined effect of oxazole compounds (I) with other drugs.

FIG. 2 is a graph representing the effect of oxazole compounds (I) on intracellular parasitic *mycobacterium tuberculosis*.

BEST MODE FOR CARRYING OUT THE INVENTION

Figure 1:
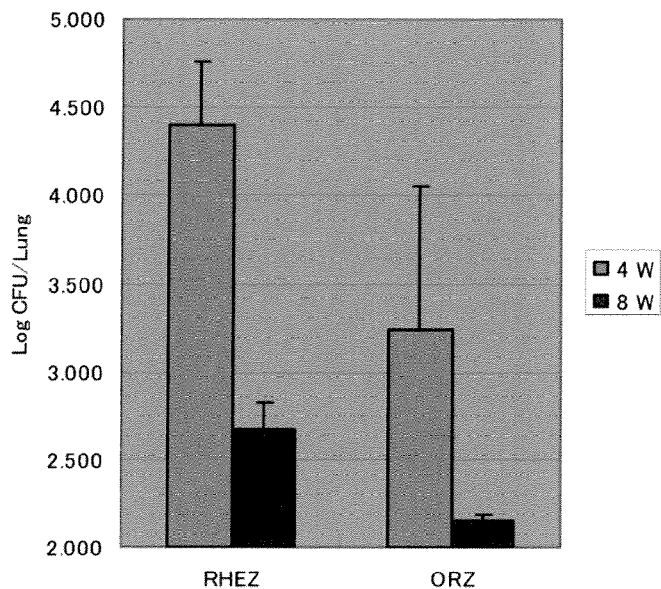
FIG. 1-1 is a graph representing the results of in vivo experiment for combined effect of oxazole compounds (I) with other drugs.

Oxazole compounds (I) used in the antituberculous therapeutic drugs of the present invention are at least one selected from the group consisting of 2,3-dihydro-6-nitroimidazo[2,1-b]oxazole compounds represented by general formula (1) described above (wherein, $R^1$-$R^8$ and n are as described above), optically active forms thereof and pharmacologically acceptable salts thereof.

wherein, a C1-6 alkyl group may include linear or branched alkyl groups composed of 1 to 6 carbon atoms, more specifically, for example, a methyl group, an ethyl group, an n-propyl group, an isopropyl group, an n-butyl group, an isobutyl group, a tert-butyl group, a sec-butyl group, an n-pentyl group, a neopentyl group, an n-hexyl group, an isohexyl group, a 3-methylpentyl group.

A halogen atom may include fluorine, chlorine, bromine and iodine atoms.

An optionally halogen-substituted C1-6 alkyl group is a linear or branched alkyl group composed of 1 to 6 carbon atoms defined above or the alkyl group substituted with 1-7 a halogen atom, and examples may include: a methyl group, ethyl group, n-propyl group, isopropyl group, n-butyl group, isobutyl group, tert-butyl group, sec-butyl group, n-pentyl group, neopentyl group, n-hexyl group, isohexyl group, 3-methylpentyl group, fluoromethyl group, difluoromethyl group, trifluoromethyl group, chloromethyl group, dichloromethyl group, trichloromethyl group, bromomethyl group, dibromomethyl group, dichlorofluoromethyl group, 2,2,2-trifluoroethyl group, pentafluoroethyl group, 2-chloroethyl group, 3,3,3-trifluoropropyl group, heptafluoropropyl group, heptafluoroisopropyl group, 3-chloropropyl group, 2-chloropropyl group, 3-bromopropyl group, 4,4,4-trifluorobutyl group, 4,4,4,3,3-pentafluorobutyl group, 4-chlorobutyl group, 4-bromobutyl group, 2-chlorobutyl group, 5,5,5-trifluoropentyl group, 5-chloropentyl group, 6,6,6-trifluorohexyl group, and 6-chlorohexyl group.

A C1-6 alkoxy group is a group composed of a C1-6 alkyl group defined above and an oxygen atom, and examples may include: a methoxy group, an ethoxy group, an n-propoxy group, an isopropoxy group, an n-butoxy group, an isobutoxy group, a tert-butoxy group, a sec-butoxy group, an n-pentoxy group, a neopentoxy group, an n-hexyloxy group, an isohexyloxy group, a 3-methylpentoxy group.

An optionally halogen-substituted C1-6 alkoxy group is a C1-6 alkoxy group defined above or the alkoxy group substituted with 1-7 a halogen atom, and examples may include: a methoxy group, ethoxy group, n-propoxy group, isopropoxy group, n-butoxy group, isobutoxy group, tert-butoxy group, sec-butoxy group, n-pentoxy group, neopentoxy group, n-hexyloxy group, isohexyloxy group, 3-methylpentoxy group, fluoromethoxy group, difluoromethoxy group, trifluoromethoxy group, chloromethoxy group, dichloromethoxy group, trichloromethoxy group, bromomethoxy group, dibromomethoxy group, dichlorofluoromethoxy group, 2,2,2-trifluoroethoxy group, pentafluoroethoxy group, 2-chloroethoxy group, 3,3,3-trifluoropropoxy group, heptafluoropropoxy group, heptafluoroisopropoxy group, 3-chloropropoxy group, 2-chloropropoxy group, 3-bromopropoxy group, 4,4,4-trifluorobutoxy group, 4,4,4,3,3-pentafluorobutoxy group, 4-chlorobutoxy group, 4-bromobutoxy group, 2-chlorobutoxy group, 5,5,5-trifluoropentoxy group, 5-chloropentoxy group, 6,6,6-trifluorohexyloxy group, and 6-chlorohexyloxy group.

A phenoxy group at least one group selected from the group consisting of a halogen atom an optionally halogen-substituted C1-6 alkyl group and an optionally halogen-substituted C1-6 alkoxy group may be substituted on the phenyl ring) may include, for example: a phenoxy group, 2-chlorophenoxy group, 2,3-dichlorophenoxy group, 3,4-dichlorophenoxy group, 3,5-dichlorophenoxy group, 2,6-dichlorophenoxy group, 2,4-dichlorophenoxy group, 2,5-dichlorophenoxy group, 2,4,6-trichlorophenoxy group, 2-fluorophenoxy group, 2,3-difluorophenoxy group, 3,4-difluorophenoxy group, 3,5-difluorophenoxy group, 2,6-difluorophenoxy group, 2,4-difluorophenoxy group, 2,5-difluorophenoxy group, 2,4,6-trifluorophenoxy group, 2-bromophenoxy group, 2,3-dibromophenoxy group, 3,4-dibromophenoxy group, 3,5-dibromophenoxy group, 2,6-dibromophenoxy group, 2,4-dibromophenoxy group, 2,5-dibromophenoxy group, 2,4,6-tribromophenoxy group, 2-methylphenoxy group, 2,3-dimethylphenoxy group, 3,4-dimethylphenoxy group, 3,5-dimethylphenoxy group, 2,6-dimethylphenoxy group, 2,4-dimethylphenoxy group, 2,5-dimethylphenoxy group, 2,4,6-trimethylphenoxy group, 3,5-ditrifluoromethylphenoxy group, 2,4,6-trifluoromethylphenoxy group, 2-trifluoromethylphenoxy group, 3-trifluoromethylphenoxy group, 4-trifluoromethylphenoxy group, 2-trifluorotnethoxyphenoxy group, 3-trifluoromethoxyphenoxy group, 4-trifluoromethoxyphenoxy group, 3-methoxyphenoxy group, 2,3-dimethoxyphenoxy group, 3,4-dimethoxyphenoxy group, 3,5-dimethoxyphenoxy group, 2,6-dimethoxyphenoxy group, 2,4-dimethoxyphenoxy group, 2,5-dimethoxyphenoxy group, 2,4,6-trimethoxyphenoxy group, 2,6-ditrifluoromethoxyphenoxy group, 2,3,4-trifluoromethoxyphenoxy group, and 2-trifluoromethyl-3-trifluoromethoxyphenoxy group (1-3 groups selected from the group consisting of a halogen atom an optionally halogen-substituted C1-6 alkyl group and an optionally halogen-substituted C1-6 alkoxy group may be substituted on the phenyl ring).

A phenyl C1-6 alkoxy group (at least one group selected from the group consisting of a halogen atom an optionally halogen-substituted C1-6 alkyl group and an optionally halogen-substituted C1-6 alkoxy group may be substituted on the phenyl ring) may include, for example: a benzyloxy group, 1-phenylethoxy group, 2-phenylethoxy group, 3-phenylpropoxy group, 2-phenylpropoxy group, 4-phenylbutoxy group, 5-phenylpentyloxy group, 4-phenylpentyloxy group, 6-phenylhexyloxy group, 2-chlorobenzyloxy group, 2,3-dichlorobenzyloxy group, 3,4-dichlorobenzyloxy group, 3,5-dichlorobenzyloxy group, 2,6-dichlorobenzyloxy group, 2,4-dlchlorobenzyloxy group, 2,5-dichlorobenzyloxy group, 2,4,6-triahlorobenzyloxy group, 2-fluorobenzyloxy group, 2,3-dLfluorobenzyloxy group, 3,4-difluorobenzyloxy grout, 3,5-difluorobenzyloxy group, 2,6-difluorobenzyloxy group, 2,4-difluorobenzyloxy group, 2,5-difluorobenzyloxy group, 2,4,6-trifluorobenzyloxy group, 2-bromobenzyloxy group, 2,3-dibromobenzyloxy group, 3,4-dibromobenzyloxy group, 3,5-dibromobenzyloxy group, 2,6-dibromobenzyloxy group, 2,4-dibromobenzyloxy group, 2,5-dibromobenzyloxy group, 2,4,6-tribromobenzyloxy group, 2-methylbenzyloxy group, 2,3-dimethylbenzyloxy group, 3,4-dimethylbenzyloxy group, 3,5-dimethylbenzyloxy group, 2,6-dimethylbenzyloxy group, 2,4-dimethylbenzyloxy group, 2,5-dimethylbenzyloxy group, 2,4,6-trimethylbenzyloxy group, 3,5-ditrifluoromethylbenzyloxy group, 2,4,6-trifluoromethylbenzyloxy group, 2-trifluoromethylbenzyloxy group, 3-trifluoromethylbenzyloxy group, 4-trifluoromethylbenzyloxy group, 2-trifluoromethoxybenzyloxy group, 3-trifluoromethoxybenzyloxy group, 4-trifluoromethoxybenzyloxy group, 3-methoxybenzyloxy group, 2,3-dimethoxybenzyloxy group, 3,4-dimethoxybenzyloxy group, 3,5-dimethoxybenzyloxy group, 2,6-dimethoxybenzyloxy group, 2,4-dimethoxybenzyloxy group, 2,5-dimethoxybenzyloxy group, 2,4,6-trimethoxybenzyloxy group, 2,6-ditrifluoromethoxybenzyloxy group, 2,3,4-trifluoromethoxybenzyloxy group, 1-(2-chlorophenyl)ethoxy group, 1-(3-chlorophenyl)ethoxy group, 1-(4-chlorophenyl)ethoxy group, 2-(2-chlorophenyl)ethoxy group, 2-(3-chlorophenyl)ethoxy group, 2-(4-chlorophenyl)ethoxy group, 1-(2-fluorophenyl)ethoxy group, 1-(3-fluorophenyl)ethoxy group, 1-(4-fluorophenyl)ethoxy group, 2-(2-fluorophenyl)ethoxy group, 2-(3-fluorophenyl)ethoxy group, 2-(4-fluorophenyl)ethoxy group, 1-(2-bromophenyl)ethoxy group, 1-(3-bromophenyl)ethoxy group, 1-(4-bromophenyl)ethoxy group, 2-(2-bromophenyl)ethoxy group, 2-(3-bromophenyl)ethoxy group, 2-(4-bromophenyl)ethoxy group, 1-(2-trifluoromethylphenyl)ethoxy group, 1-(3-trifluoromethylphenyl)ethoxy group, 1-(4-trifluoromethylphenyl)ethoxy group, 1-(2-trifluoromethoxyphenyl)ethoxy group, 1-(3-trifluoromethoxyphenyl)ethoxy group, 1-(4-trifluoromethoxyphenyl)ethoxy group, 2-(2-trifluoromethylphenyl)ethoxy group, 2-(3-trifluoromethylphenyl)ethoxy group, 2-(4-trifluoromethylphenyl)ethoxy group, 2-(2-trifluoromethoxyphenyl)ethoxy group, 2-(3-trifluoromethoxyphenyl)ethoxy group, 2-(4-trifluoromethoxyphenyl)ethoxy group, 3-(2-chlorophenyl)propoxy group, 3-(3-chlorophenyl)propoxy group, 3-(4-chlorophenyl)propoxy group, 3-(2-fluorophenyl)propoxy group, 3-(3-fluorophenyl)propoxy group, 3-(4-fluorophenyl)propoxy group, 3 (2-bromophenyl)propoxy group, 3-(3-bromophenyl)propoxy group, 3-(4-bromophenyl)propoxy group, 3-(2-trifluoromethylphenyl)propoxy group, 3-(3-trifluoromethylphenyl)propoxy group, 3-(4-trifluoromethylphenyl)propoxy group, 3-(2-trifluoromethylphenyl)propoxy group, 3-(3-trifluoromethoxyphenyl)propoxy group, 3-(4-trifluoromethoxyphenyl)propoxy group, 4-(3-chlorophenyl)butoxy group, 4-(3-fluorophenyl)butoxy group, 4-(3-bromophenyl)butoxy group, 4-(3-trifluoromethylphenyl)butoxy group, 5-(4-chlorophenyl)pentyloxy group, 4-(4-chlorophenyl)pentyloxy group, 5-(4-fluorophenyl)pentyloxy group, 4-(4-fluorophenyl)pentyloxy group, 5-(4-bromophenyl)pentyloxy group, 4-(4-bromophenyl)pentyloxy group, 5-(4-trifluoromethylphenyl)pentyloxy group, 4-(4-tfifluoromethylphenyl)pentyloxy group, 4-(4-trifluoromethoxyphenyl)pentyloxy group, 6-(3-chlorophenyl)hexyloxy group, 6-(4-chlorophenyl)hexyloxy group, 6-(3-fluorophenyl)hexyloxy group, 6-(4-fluorophenyl)hexyloxy group, 6-(3-bromophenyl)hexyloxy group, 6-(4-bromophenyl)hexyloxy group, 6-(3-trifluoromethylphenyl)hexyloxy group, 6-(4-trifluoromethylphenyl)hexyloxy group, 6-(4-trifluoromethoxyphenyl)hexyloxy group, and 2-trifluoromethyl-3-trifluoromethoxylienzyloxy group (1-3 groups selected from the group consisting of a halogen atom an optionally halogen-substituted C1-6 alkyl group and an optionally halogen-substituted C1-6 alkoxy group may be substituted on the phenyl ring).

A phenyl group (at least one group selected from the group consisting of a halogen atom an optionally halogen-substituted C1-6 alkyl group and an optionally halogen-substituted C1-6 alkoxy group may be substituted on the phenyl ring) may include, for example: a phenyl group, 2-chlorophenyl group, 2,3-dichlorophenyl group, 3,4-dichlorophenyl group, 3,5-dichlorophenyl group, 2,6-dichlorophenyl group, 2,4-dichlorophenyl group, 2,5-dichlorophenyl group, 2,4,6-trichlorophenyl group, 2-fluorophenyl group, 2,3-difluorophenyl group, 3,4-difluorophenyl group, 3,5-difluorophenyl group, 2,6-difluorophenyl group, 2,4-difluorophenyl group, 2,5-difluorophenyl group, 2,4,6-trifluorophenyl group, 2-bromophenyl group, 2,3-dibromophenyl group, 3,4-dibromophenyl group, 3,5-dibromophenyl group, 2,6-dibromophenyl group, 2,4-dibromophenyl group, 2,5-dibromophenyl group, 2,4,6-tribromophenyl group, 2-methylphenyl group, 2,3-dimethylphenyl group, 3,4-dimethylphenyl group, 3,5-dimethylphenyl group, 2,6-dimethylphenyl group, 2,4-dimethylphenyl group, 2,5-dimethylphenyl group, 2,4,6-trimethylphenyl group, 3,5-ditrifluoromethylphenyl group, 2,4,6-trifluoromethylphenyl group, 2-trifluoromethylphenyl group, 3-trifluoromethylphenyl group, 4-trifluoromethylphenyl group, 2-trifluoromethoxyphenyl group, 3-trifluoromethoxyphenyl group, 4-trifluoromethoxyphenyl group, 3-methoxyphenyl group, 2,3-dimethoxyphenyl group, 3,4-dimethoxyphenyl group, 3,5-dimethoxyphenyl group, 2,6-dimethoxyphenyl group, 2,4-dimethoxyphenyl group, 2,5-dimethoxyphenyl group, 2,4,6-trimethoxyphenyl group, 2,6-ditrifluoromethoxyphenyl group, 2,3,4-trifluoromethoxyphenyl group, and 2-trifluoromethyl-3-trifluoromethoxyphenyl group (1-3 groups selected from the group consisting of a halogen atom an optionally halogen-substituted C1-6 alkyl group and an optionally halogen-substituted C1-6 alkoxy group may be substituted on the phenyl ring).

A phenyl C1-6 alkyl group (at least one group selected from the group consisting of a halogen atom an optionally halogen-substituted C1-6 alkyl group and an optionally halogen-substituted C1-6 alkoxy group may be substituted on the phenyl ring) may include, for example: a benzyl group, 1-phenethyl group, 2-phenethyl group, 3-phenylpropyl group, 2-phenylpropyl group, 4-phenylbutyl group, 5-phenylpentyl group, 4-phenylpentyl group, 6-phenylhexyl group, 2-chlorobenzyl group, 2,3-dichlorobenzyl group, 3,4-dichlorobenzyl group, 3,5-dichlorobenzyl group, 2,6-dichlorobenzyl group, 2,4-dichlorobenzyl group, 2,5-dichlorobenzyl group, 2,4,6-trichlorobenzyl group, 2-fluorobenzyl group, 2,3-difluorobenzyl group, 3,4-difluorobenzyl group, 3,5-difluorobenzyl group, 2,6-difluorobenzyl group, 2,4-difluorobenzyl group, 2,5-difluorobenzyl group, 2,4,6-trifluorobenzyl group, 2-bromobenzyl group, 2,3-dibromobenzyl group, 3,4-dibromobenzyl group, 3,5-dibromobenzyl group, 2,6-dibromobenzyl group, 2,4-dibromobenzyl group, 2,5-dibromobenzyl group, 2,4,6-tribromobenzyl group, 2-methylbenzyl group, 2,3-dimethylbenzyl group, 3,4-dimethylbenzyl group, 3,5-dimethylbenzyl group, 2,6-dimethylbenzyl group, 2,4-dimethylbenzyl group, 2,5-dimethylbenzyl group, 2,4,6-trimethylbenzyl group, 3,5-ditrifluoromethylbenzyl group, 2,4,6-trifluoromethylbenzyl group, 2-trifluoromethylbenzyl group, 3-trifluoromethylbenzyl group, 4-trifluoromethylbenzyl group, 2-trifluoromethoxybenzyl group, 3-trifluoromethoxybenzyl group, 4-trifluoromethoxybenzyl group, 3-methoxybenzyl group, 2,3-dimethoxybenzyl group, 3,4-dimethoxybenzyl group, 3,5-dimethoxybenzyl group, 2,6-dimethoxybenzyl group, 2,4-dimethoxybenzyl group, 2,5-dimethoxybenzyl group, 2,4,6-trimethoxybenzyl group, 2,6-ditrifluoromethoxybenzyl group, 2,3,4-trifluoromethoxybenzyl group, 1-(2-chlorophenyl)ethyl group, 1-(3-chlorophenyl)ethyl group, 1-(4-chlorophenyl)ethyl group, 2-(2-chlorophenyl)ethyl group, 2-(3-chlorophenyl)ethyl group, 2-(4-chlorophenyl)ethyl group, 1-(2-fluorophenyl)ethyl group, 1-(3-fluorophenyl)ethyl group, 1-(4-fluorophenyl)ethyl group, 2-(2-fluorophenyl)ethyl group, 2-(3-fluorophenyl)ethyl group, 2-(4-fluorophenyl)ethyl group, 1-(2-bromophenyl)ethyl group, 1-(3-bromophenyl)ethyl group, 1-(4-bromophenyl)ethyl group, 2-(2-bromophenyl)ethyl group, 2-(3-bromophenyl)ethyl group, 2-(4-bromophenyl)ethyl group, 1-(2-trifluoromethylphenyl)ethyl group, 1-(3-trifluoromethylphenyl)ethyl group, 1-(4-trifluoromethylphenyl)ethyl group, 1-(2-trifluoromethoxyphenyl)ethyl group, 1-(3-trifluoromethoxyphenyl)ethyl group, 1-(4-trifluoromethoxyphenyl)ethyl group, 2-(2-trifluoromethylphenyl)ethyl group, 2-(3-trifluoromethylphenyl)ethyl group, 2-(4-trifluoromethylphenyl)ethyl group, 2-(2-trifluoromethoxyphenyl)ethyl group, 2-(3-trifluoromethoxyphenyl)ethyl group, 2-(4-trifluoromethoxyphenyl)ethyl group, 3-(2-chlorophenyl)propyl group, 3-(3-chlorophenyl)propyl group, 3-(4-chlorophenyl)propyl group, 3-(2-fluorophenyl)propyl group, 3-(3-fluorophenyl)propyl group, 3-(4-fluorophenyl)propyl group, 3-(2-bromophenyl)propyl group, 3-(3-bromophenyl)propyl group, 3-(4-bromophenyl)propyl group, 3-(2-trifluoromethylphenyl)propyl group, 3-(3-trifluoromethylphenyl)propyl group, 3-(4-trifluoromethylphenyl)propyl group, 3-(2-trifluoromethylphenyl)propyl group, 3-(3-trifluoromethoxyphenyl)propyl group, 3-(4-trifluoromethoxyphenyl)propyl group, 4-(3-chlorophenyl)butyl group, 4-(3-fluorophenyl)butyl group, 4-(3-bromophenyl)butyl group, 4-(3-trifluoromethylphenyl)butyl group, 5-(4-chlorophenyl)pentyl group, 4-(4-chlorophenyl)pentyl group, 5-(4-fluorophenyl)pentyl group, 4-(4-fluorophenyl)pentyl group, 5-(4-bromophenyl)pentyl group, 4-(4-bromophenyl)pentyl group, 5-(4-trifluoromethylphenyl)pentyl group, 4-(4-trifluoromethylphenyl)pentyl group, 4-(4-trifluoromethoxyphenyl)pentyl group, 6-(3-chlorophenyl)hexyl group, 6-(4-chlorophenyl)hexyl group, 6-(3-fluorophenyl)hexyl group, 6-(4-fluorophenyl)hexyl group, 6-(3-bromophenyl)hexyl group, 6-(4-bromophenyl)hexyl group, 6-(3-trifluoromethylphenyl)hexyl group, 6-(4-trifluoromethylphenyl)hexyl group, 6-(4-trifluoromethoxyphenyl)hexyl group, and 2-trifluoromethyl-3-trifluoromethoxybenzyl group (1-3 groups selected from the group consisting of a halogen atom an optionally halogen-substituted C1-6 alkyl group and an optionally halogen-substituted C1-6 alkoxy group may be substituted on the phenyl ring).

A phenoxy C1-6 alkyl group (at least one group selected from the group consisting of a halogen atom an optionally halogen-substituted C1-6 alkyl group and an optionally halogen-substituted C1-6 alkoxy group may be substituted on the phenyl ring) is a group composed of a phenoxy group unsubstituted or substituted with 1-5, preferably 1-3 groups selected from the group consisting of an optionally halogen-substituted C1-6 alkyl group and an optionally halogen-substituted C1-6 alkoxy group and halogen as defined above and a C1-6 alkyl group, and may include, for example: a phenoxymethyl group, 2-phenoxyethyl group, 3-phenoxypropyl group, 4-phenoxybutyl group, 5-phenoxypentyl group, 6-phenoxyhexyl group, 4-fluorophenoxymethyl group, 2-fluoro-4-bromophenoxymethyl group, 4-chloro-3-fluorophenoxymethyl group, 2,3,4-trichlorophenoxymethyl group, 3,4,5-trichlorophenoxymethyl group, 2,4,6-trichlorophenoxymethyl group, 4-isopropylphenoxymethyl group, 4-n-butylphenoxymethyl group, 4-methylphenoxymethyl group, 2-methylphenoxymethyl group, 3-methylphenoxymethyl group, 2,4-dimethylphenoxymethyl group, 2,3-dimethylphenoxymethyl group, 2,6-dimethylphenoxymethyl group, 3,5-dimethylphenoxymethyl group, 2,5-dimethylphenoxymethyl group, 2,4,6-trimethylphenoxymethyl group, 3,5-ditrifluoromethylphenoxymethyl group, 2,3,4,5,6-pentafluorophenoxymethyl group, 4-isopropoxyphenoxymethyl group, 4-n-butoxyphenoxymethyl group, 4-methoxyphenoxymethyl group, 2-methoxyphenoxymethyl group, 3-methoxyphenoxymethyl group, 2,4-dimethoxyphenoxymethyl group, 2,3-dimethoxyphenoxymethyl group, 2,6-dimethoxyphenoxymethyl group, 3,5-dimethoxyphenoxymethyl group, 2,5-dimethoxyphenoxymethyl group, 2,4,6-trimethoxyphenoxymethyl group, 3,5-ditrifluoromethoxyphenoxymethyl group, 2-isopropoxyphenoxymethyl group, 3-chloro-4-methoxyphenoxymethyl group, 2-chloro-4-trifluoromethoxyphenoxymethyl group, 3-methyl-4-fluorophenoxymethyl group, 4-bromo-3-trifluoromethylphenoxymethyl group, 2-(4-fluorophenoxy)ethyl group, 3-(4-fluorophenoxy)propyl group, 4-(4-fluorophenoxy)butyl group, 5-(4-fluorophenoxy)pentyl group, 6-(4-fluorophenoxy)hexyl group, 4-chlorophenoxymethyl group, 2-(4-chlorophenoxy)ethyl group, 3-(4-chlorophenoxy)propyl group, 4-(4-chlorophenoxy)butyl group, 5-(4-chlorophenoxy)pentyl group, 6-(4-chlorophenoxy)hexyl group, 4-methylphenoxymethyl group, 2-(4-methylphenoxy)ethyl group, 3-(4-methylphenoxy)propyl group, 4-(4-methylphenoxy)butyl group, 5-(4-methylphenoxy)pentyl group, 6-(4-methylphenoxy)hexyl group, 4-trifluoromethylphenoxymethyl group, 2-(4-trifluoromethylphenoxy)ethyl group, 3-(4-trifluoromethylphenoxy)propyl group, 4-(4-trifluoromethylphenoxy)butyl group, 5-(4-trifluoromethylphenoxy)pentyl group, 6-(4-trifluoromethylphenoxy)hexyl group, 4-trifluoromethoxyphenoxymethyl group, 2-(4-trifluoromethoxyphenoxy)ethyl group, 3-(4-trifluoromethoxyphenoxy)propyl group, 4-(4-trifluoromethoxyphenoxy)butyl group, 5-(4-trifluoromethoxyphenoxy)pentyl group, 6-(4-trifluoromethoxyphenoxy)hexyl group, 2-(4- methoxyphenoxy)ethyl group, 3-(4-methoxyphenoxy)propyl group, 4-(4-methoxyphenoxy)butyl group, 5-(4-methoxyphenoxy)pentyl group, and 6-(4-methoxyphenoxy)hexyl group.

A benzofuryl C1-6 alkyl group (at least one group selected from the group consisting of a halogen atom an optionally halogen-substituted C1-6 alkyl group and an optionally halogen-substituted C1-6 alkoxy group may be substituted on the benzofuran ring) may include, for example: a benzofuryl C1-6 alkyl group (at least one group selected from the group consisting of a halogen atom an optionally halogen-substituted C1-6 alkyl group and an optionally halogen-substituted C1-6 alkoxy group may be substituted on the benzofuran ring) wherein, the alkyl moiety is a C1-6 linear or branched alkyl group such as: a [(2-, 3-, 4-, 5-, 6-, or 7-)benzofuryl]methyl group, 1-[(2-, 3-, 4-, 5-, 6-, or 7-)benzofuryl]ethyl group, 2-[(2-, 3-, 4-, 5-, 6-, or 7-)benzofuryl]ethyl group, 3-[(2-, 3-, 4-, 5-, 6-, or 7-)benzofuryl]propyl group, 2-[(2-, 3-, 4-, 5-, 6-, or 7-)benzofuryl]propyl group, 4-[(2-, 3-, 4-, 5-, 6-, or 7-)benzofuryl]butyl group, 5-[(2-, 3-, 4-, 5-, 6-, or 7-)benzofuryl]pentyl group, 4-[(2->3-, 4-, 5-, 6-, or 7-)benzofuryl]pentyl group, 6-[(2-, 3-, 4-, 5-, 6-, or 7-)benzofuryl]hexyl group, 2-chloro-3-[(2-, 3-, 4-, 5-, 6-, or 7-)benzofuryl]propyl group, 1,1-dichloro-2-[(2-, 3-, 4-, 5-, 6-, or 7-)benzofuryl]ethyl group, 2-fluoro-3-[(2-, 3-, 4-, 5-, 6-, or 7-)benzofuryl]propyl group, 1,1-difluoro-2-[(2-, 3-, 4-, 5-, 6-, or 7-)benzofuryl]ethyl group, 2-bromo-3-[(2-, 3-, 4-, 5-, 6-, or 7-)benzofuryl]propyl group, 1,1-dibromo-2-[(2-, 3-, 4-, 5-, 6-, or 7-)benzofuryl]ethyl group, 2-methyl-3-[(2-, 3-, 4-, 5-, 6-, or 7-)benzofuryl]propyl group, 1,1-dimethyl-2-[(2-, 3-, 4-, 5-, 6-, or 7-)benzofuryl]ethyl group, 2-trifluoromethyl-(3-, 4-, 5-, 6-, or 7-)benzofurylmethyl group, 5-trifluoromethyl-(2-, 3-, 4-, 6-, or 7-)benzofurylmethyl group, 4-methyl-(2-, 3-, 5-, 6-, or 7-)benzofurylmethyl group, 2,4-dimethyl-(3-, 5-, 6-, or 7-)benzofurylmethyl group, 2,4,6-trimethyl-(3-, 5-, or 7-)benzofurylmethyl group, 4-trifluoromethyl-(2-, 3-, 5-, 6-, or 7-)benzofurylmethyl group, 6-trifluoromethyl-(2-, 3-, 4-, 5-, or 7-)benzofurylmethyl group, 2-methoxy-3-[(2-, 3-, 4-, 5-, 6-, or 7-)benzofuryl]propyl group, 1,1-dimethoxy-2-[(2-, 3-, 4-, 5-, 6-, or 7-)benzofuryl]ethyl group, 2-trifluoromethoxy-(3-, 4-, 5-, 6-, or 7-)benzofurylmethyl group, 5-trifluoromethoxy-(2-, 3-, 4-, 6-, or 7-)benzofurylmethyl group, 4-methoxy-(2-, 3-, 5-, 6-, or 7-)benzofurylmethyl group, 2,4-dimethoxy-(3-, 5-, 6-, or 7-)benzofurylmethyl group, 2,4,6-trimethoxy-(3-, 5-, or 7-)benzofurylmethyl group, 4-trifluoromethoxy-(2-, 3-, 5-, 6-, or 7-)benzofurylmethyl group, and 6-trifluoromethoxy-(2-, 3-, 4-, 5-, or 7-)benzofurylmethyl group.

A phenyl C2-10 alkenyl group (at least one, group selected from the group consisting of a halogen atom an optionally halogen-substituted C1-6 alkyl group and an optionally halogen-substituted C1-6 alkoxy group may be substituted on the phenyl ring) includes both trans and cis forms, and 1-5, preferably, 1-3 groups selected from the group consisting of a halogen atom an optionally halogen-substituted C1-6 alkyl group and an optionally halogen-substituted C1-6 alkoxy group may be substituted on the phenyl ring which composes the phenyl C2-10 alkenyl group. Examples of such a phenyl C2-10 alkenyl group may include, for example; a 3-phenyl-2-propenyl group (conventional name: a cinnamyl group), a 4-phenyl-2-butenyl group, 4-phenyl-3-butenyl group, 5-phenyl-4-pentenyl group, 5-phenyl-3-pentenyl group, 6-phenyl-5-hexenyl group, 6-phenyl-4-hexenyl group, 6-phenyl-3-hexenyl group, 4-phenyl-1,3-butadienyl group, 6-phenyl-1,3,5-hexatrienyl group, 2-n-pentyl-3-phenyl-2-propenyl group, 9-phenyl-2-nonenyl group, 10-phenyl-2-decenyl group, 8-phenyl-1,3-octadienyl group, 9-phenyl-1,3,5-nonatrienyl group, 10-phenyl-2,4,6-decatrienyl group, 3-(2-chlorophenyl)-2-propenyl group, 4-(3-fluorophenyl)-2-butenyl group, 4-(4-bromophenyl)-3-butenyl group, 5-(3-chlorophenyl)-4-pentenyl group, 5-(4-fluorophenyl)-3-pentenyl group, 6-(2-bromophenyl)-5-hexenyl group, 6-(4-chlorophenyl)-4-hexenyl group, 6-(2-fluorophenyl)-3-hexenyl group, 4-(2-chlorophenyl)-1,3-butadienyl group, 6-(3-fluorophenyl)-1,3,5-hexatrienyl group, 2-n-pentyl-3-(3-bromophenyl)-2-propenyl group, 9-(3-chlorophenyl)-2-nonenyl group, 10-(4-fluorophenyl)-2-decenyl group, 8-(4-bromphenyl)-1,3-octadienyl group, 9-(4-chlorophenyl)-1,3,5-nonatrienyl group, 10-(2-fluorophenyl)-2,4,6-decatrienyl group, 3-(2-methylphenyl)-2-propenyl group, 3-(2,3-dimethylphenyl)-2-propenyl group, 3-(3,4-dimethylphenyl)-2-propenyl group, 3-(3,5-dimethylphenyl)-2-propenyl group, 3-(2,6-dimethylphenyl)-2-propenyl group, 3-(2,4-dimethylphenyl)-2-propenyl group, 3-(2,5-dimethylphenyl)-2-propenyl group, 3-(2,4,6-trimethylphenyl)-2-propenyl group, 3-(3,5-ditrifluoromethylphenyl)-2-propenyl group, 3-(2,4,6-trifluoromethylphenyl)-2-propenyl group, 3-(2-trifluoromethylphenyl)-2-propenyl group, 3-(3-trifluoromethylphenyl)-2-propenyl group, 3-(4-trifluoromethylphenyl)-2-propenyl group, 3-(2-trifluoromethoxyphenyl)-2-propenyl group, 3-(3-trifluoromethoxyphenyl)-2-propenyl group, 3-(4-trifluoromethoxyphenyl)-2-propenyl group, 3-(3-methoxyphenyl)-2-propenyl group, 3-(2,3-dimethoxyphenyl)-2-propenyl group, 3-(3,4-dimethoxyphenyl)-2-propenyl group, 3-(3,5-dimethoxyphenyl)-2-propenyl group, 3-(2,6-dihethoxyphenyl)-2-propenyl group, 3-(2,4-dimethoxyphenyl)-2-propenyl group, 3-(2,5-dimethoxyphenyl)-2-propenyl group, 3-(2,4,6-trimethoxyphenyl)-2-propenyl group, 3-(2,6-ditrifluoromethoxyphenyl)-2-propenyl group, 3-(2,3,4-trifluoromethoxyphenyl)-2-propenyl group, 3-(2-trifluoromethyl-3-trifluoromethoxyphenyl)-2-propenyl group, 4-(3-trifluoromethylphenyl)-2-butenyl group, 4-(4-trifluoromethylphenyl)-3-butenyl group, 5-(3-trifluoromethylphenyl)-4-pentenyl group, 5-(4-trifluoromethylphenyl)-3-pentenyl group, 6-(2-trifluoromethylphenyl)-5-hexenyl group, 6-(4-trifluoromethylphenyl)-4-hexenyl group, 6-(2-trifluoromethylphenyl)-3-hexenyl group, 4-(2-trifluoromethylphenyl)-1,3-butadienyl group, 6-(3-trifluoromethylphenyl)-1,3,5-hexatrienyl group, 2-n-pentyl-3-(3-trifluoromethylphenyl)-2-propenyl group, 9-(3-trifluoromethylphenyl)-2-nonenyl group, 10-(4-trifluoromethylphenyl)-2-decenyl group, 8-(4-trifluoromethylphenyl)-1,3-octadienyl group, 9-(4-trifluoromethylphenyl)-1,3,5-nonatrienyl group, and 10-(2-trifluoromethylphenyl)-2,4,6-decatrienyl group. These are all an alkenyl group wherein 1-2 phenyl groups are substituted on the C2-10 alkenyl group with 2-10 carbon atoms and 1-3 double bonds (at least one group selected from the group consisting of a halogen atom an optionally halogen-substituted C1-6 alkyl group and an optionally halogen-substituted C1-6 alkoxy group may be substituted on the phenyl ring).

A biphenyl C1-6 alkyl group (at least one group selected from the group consisting of a halogen atom an optionally halogen-substituted C1-6 alkyl group and an optionally halogen-substituted C1-6 alkoxy group may be substituted on the phenyl ring) may include, for example: a biphenyl C1-6 alkyl group (1-3 groups selected from the group consisting of a halogen atom an optionally halogen-substituted C1-6 alkyl group and an optionally halogen-substituted C1-6 alkoxy group may be substituted on the phenyl ring) such as: a 4-biphenylmethyl group, 1-(4-biphenyl)ethyl group, 2-(4-biphenyl)ethyl group, 3-(4-biphenyl)propyl group, 2-(4-biphenyl)propyl group, 4(4-biphenyl)butyl group, 5-(4-biphenyl)pentyl group, 4-(4-biphenyl)pentyl group, 6-(4-biphenyl)hexyl group, 2'-chloro-4-biphenylmethyl group, 2',3'-dichloro-4-biphenylmethyl group, 3',4'-dichloro-4-biphenylmethyl group, 3',5'-dichloro-4-biphenylmethyl group, 2',6'-dichloro-4-biphenylmethyl group, 2',4'-dichloro-4-biphenylmethyl group, 2',5'-dichloro-4-biphenylmethyl group, 2',4',6'-trichloro-4-biphenylmethyl group, 2'-fluoro-4-biphenylmethyl group, 2',3'-difluoro-4-biphenylmethyl group, 3',4'-difluoro-4-biphenylmethyl group, 3',5'-difluoro-4-biphenylmethyl group, 2',6'-difluoro-4-biphenylmethyl group, 2',4'-difluoro-4-biphenylmethyl group, 2',5'-difluoro-4-biphenylmethyl group, 2',4',6'-trifluoro-4-biphenylmethyl group, 2'-bromo-4-biphenylmethyl group, 2',3'-dibromo-4-biphenylmethyl group, 3',4'-dibromo-4-biphenylmethyl group, 3',5'-dibromo-4-biphenylmethyl group, 2',6'-dibromo-4-biphenylmethyl group, 2',4'-dibromo-4-biphenylmethyl group, 2',5'-dibromo-4-biphenylmethyl group, 2',4',6'-tribromo-4-biphenylmethyl group, 2'-methyl-4-biphenylmethyl group, 2',3'-dimethyl-4-biphenylmethyl group, 3',4'-dimethyl-4-biphenylmethyl group, 3',5'-dimethyl-4-biphenylmethyl group, 2',6'-dimethyl-4-biphenylmethyl group, 2',4'-dimethyl-4-biphenylmethyl group, 2',5'-dimethyl-4-biphenylmethyl group, 2',4',6'-trimethyl-4-biphenylmethyl group, 3',5'-ditrifluoromethyl-4-biphenylmethyl group, 2',4',6'-trifluoromethyl-4-biphenylmethyl group, 2'-trifluoromethyl-4-biphenylmethyl group, 3'-trifluoromethyl-4-biphenylmethyl group, 4'-trifluoromethyl-4-biphenylmethyl group, 2'-trifluoromethoxy-4-biphenylmethyl group, 3'-trifluoromethoxy-4-biphenylmethyl group, 4'-trifluoromethoxy-4-biphenylmethyl group, 3'-methoxy-4-biphenylmethyl group, 2',3'-dimethoxy-4-biphenylmethyl group, 3',4'-dimethoxy-4-biphenylmethyl group, 3',5'-dimethoxy-4-biphenylmethyl group, 2',6'-dimethoxy-4-biphenylmethyl group, 2',4'-dimethoxy-4-biphenylmethyl group, 2',5'-dimethoxy-4-biphenylmethyl group, 2',4',6'-trimethoxy-4-biphenylmethyl group, 2',6'-ditrifluoromethoxy-4-biphenylmethyl group, 2',3',4'-trifluoromethoxy-4-biphenylmethyl group, 1-(2'-chloro-4-biphenyl)ethyl group, 1-(3'-chloro-4-biphenyl)ethyl group, 1-(4'-chloro-4-biphenyl)ethyl group, 2-(2'-chloro-4-biphenyl)ethyl group, 2-(3'-chloro-4-biphenyl)ethyl group, 2-(4'-chloro-4-biphenyl)ethyl group, 1-(2'-fluoro-4-biphenyl)ethyl group, 1-(3'-fluoro-4-biphenyl)ethyl group, 1-(4'-fluoro-4-biphenyl)ethyl-group, 2-(2'-fluoro-4-biphenyl)ethyl group, 2-(3'-fluoro-4-biphenyl)ethyl group, 2-(4'-fluoro-4-biphenyl)ethyl group, 1-(2'-bromo-4-biphenyl)ethyl group, 1-(3'-bromo-4-biphenyl)ethyl group, 1-(4'-bromo-4-biphenyl)ethyl group, 2-(2'-bromo-4-biphenyl)ethyl group, 2-(3'-bromo-4-biphenyl)ethyl group, 2-(4'-bromo-4-biphenyl)ethyl group, 1-(2'-trifluoromethyl-4-biphenyl)ethyl group, 1-(3'-trifluoromethyl-4-biphenyl)ethyl group, 1-(4'-trifluoromethyl-4-biphenyl)ethyl group, 1-(2'-trifluoromethoxy-4-biphenyl)ethyl group, 1-(3'-trifluoromethoxy-4-biphenyl)ethyl group, 1-(4'-trifluoromethoxy-4-biphenyl)ethyl group, 2-(2'-trifluoromethyl-4-biphenyl)ethyl group, 2-(3'-trifluoromethyl-4-biphenyl)ethyl group, 2-(4'-trifluoromethyl-4-biphenyl)ethyl group, 2-(2'-trifluoromethoxy-4-biphenyl)ethyl group, 2-(3'-trifluoromethoxy-4-biphenyl)ethyl group, 2-(4'-trifluoromethoxy-4-biphenyl)ethyl group, 3-(2'-chloro-4-biphenyl)propyl group, 3-(3'-chloro-4-biphenyl)propyl group, 3-(4'-chloro-4-biphenyl)propyl group, 3-(2'-fluoro-4-biphenyl)propyl group, 3-(3'-fluoro-4-biphenyl)propyl group, 3-(4'-fluoro-4-biphenyl)propyl group, 3-(2'-bromo-4-biphenyl)propyl group, 3-(3'-bromo-4-biphenyl)propyl group, 3-(4'-bromo-4-biphenyl)propyl group, 3-(2'-trifluoromethyl-4-biphenyl)propyl group, 3-(3'-trifluoromethyl-4-biphenyl)propyl group, 3-(4'-trifluoromethyl-4-biphenyl)propyl group, 3-(2'-trifluoromethyl-4-biphenyl)propyl group, 3-(3'-trifluoromethoxy-4-biphenyl)propyl group, 3-(4'-trifluoromethoxy-4-biphenyl)propyl group, 4-(3'-chloro-4-biphenyl)butyl group, 4-(3'-fluoro-4-biphenyl)butyl group, 4-(3'-bromo-4-biphenyl)butyl group, 4-(3'-trifluoromethyl-4-biphenyl)butyl group, 5-(4'-chloro-4-biphenyl)pentyl group, 4-(4'-chloro-4-biphenyl)pentyl group, 5-(4'-fluoro-4-biphenyl)pentyl group, 4-(4'-fluoro-4-biphenyl)pentyl group, 5-(4'-bromo-4-biphenyl)pentyl group, 4-(4'-bromo-4-biphenyl)pentyl group, 5-(4'-trifluoromethyl-4-biphenyl)pentyl group, 4-(4'-trifluoromethyl-4-biphenyl)pentyl group, 4-(4'-trifluoromethoxy-4-biphenyl)pentyl group, 6-(3'-chloro-4-biphenyl)hexyl group, 6-(4'-chloro-4-biphenyl)hexyl group, 6-(3'-fluoro-4-biphenyl)hexyl group, 6-(4'-fluoro-4-biphenyl)hexyl group, 6-(3'-bromo-4-biphenyl)hexyl group, 6-(4'-bromo-4-biphenyl)hexyl group, 6-(3'-trifluoromethyl-4-biphenyl)hexyl group, 6-(4'-trifluoromethyl-4-biphenyl)hexyl group, 6-(4'-trifluoromethoxy-4-biphenyl)hexyl group, and 2'-trifluoromethyl-3'-trifluoromethoxy-4-biphenylmethyl group.

Oxazole compounds represented by the general formula (1) include, for example, the following compounds:

(R)-2-methyl-6-nitro-2-{4-[4-(4-trifluoromethoxyphenoxy)piperidin-1-yl]phenoxymethyl}-2,3-dihydroimidazo[2,1-b]oxazole (hereinafter referred to as "compound (A-R)")

(S)-2-methyl-6-nitro-2-{4-[4-(4-trifluoromethoxyphenoxy)piperidin-1-yl]phenoxymethyl}-2,3-dihydroimidazo[2,1-b]oxazole (hereinafter referred to as "compound (A-S)")

(RS)-2-methyl-6-nitro-2-{4-[4-(4-trifluoromethoxyphenoxy)piperidin-1-yl]phenoxymethyl}-2,3-dihydroimidazo[2,1-b]oxazole (hereinafter referred to as "compound (A-RS)")

3-(4-trifluoromethylphenyl)-2-propenyl (R)-4-(2-methyl-6-nitro-2,3-dihydroimidazo[2,1-b]oxazol-2-ylmethyl)piperazine-1-carboxylate (hereinafter referred to as "compound (B—R)")

3-(4-trifluoromethylphenyl)-2-propenyl (S)-4-(2-methyl-6-nitro-2,3-dihydroimidazo[2,1-b]oxazol-2-ylmethyl)piperazine-1-carboxylate (hereinafter referred to as "compound (B—S)")

3-(4-trifluoromethylphenyl)-2-propenyl (RS)-4-(2-methyl-6-nitro-2,3-dihydroimidazo[2,1-b]oxazol-2-ylmethyl)piperazine-1-carboxylate (hereinafter referred to as "compound (B—RS)")

(R)-2-(4-{4-[N-(4-chlorophenyl)-N-methyl-amino]piperidin-1-yl}phenoxymethyl)-2-methyl-6-nitro-2,3-dihydroimidazo[2,1-b]oxazole (hereinafter referred as "compound (E-S)")

(RS)-2-{4-[4-(3,4-dichlorobenzyl)piperidin-1-yl]phenoxymethyl}-2-methyl-6-nitro-2,3-dihydroimidazo[2,1-b]oxazole (hereinafter referred to as "compound (E-RS)")

(R)-6-nitro-2-{4-[4-(4-trifluoromethoxyphenoxy)piperidin-1-yl]phenoxymethyl}-2,3-dihydroimidazo[2,1-b]oxazole (hereinafter referred to as "compound (F—R)")

(S)-6-nitro-2-{4-[4-(4-trifluoromethoxyphenoxy)piperidin-1-yl]phenoxymethyl}-2,37-dihydroimidazo[2,1-b]oxazole (hereinafter referred to as "compound (F-S)")

(RS)-6-nitro-2-{4-[4-(4-trifluoromethoxyphenoxy)piperidin-1-yl]phenoxymethyl}-2,3-dihydroimidazo[2,1-b]oxazole (hereinafter referred to as "compound (F-RS)")

(R)-6-(2-methyl-6-nitro-2,3-dihydroimidazo[2,1-b]oxazol-2-ylmethoxy)-2-[4-(4-trifluoromethoxybenzyl)piperazin-1-yl]benzothiazole (hereinafter referred to as "compound (G-R)")

(S)-6-(2-methyl-6-nitro-2,3-dihydroimidazo[2,1-b]oxazol-2-ylmethoxy)-2-[4-(4-trifluoromethoxybenzyl)piperazin-1-yl]benzothiazole (hereinafter referred to as "compound (G-S)")

(RS)-6-(2-methyl-6-nitro-2,3-dihydroimidazo[2,1-b]oxazol-2-ylmethoxy)-2-[4-(4-trifluoromethoxybenzyl)piperazin-1-yl]benzothiazole to as "compound (C-R)")

(S)-2-(4-{4-[N-(4-chlorophenyl)-N-methyl-amino]piperidin-1-yl}phenoxymethyl)-2-methyl-6-nitro-2,3-dihydroimidazo[2,1-b]oxazole (hereinafter referred to as "compound (C—S)")

(RS)-2-(4-{4-[N-(4-chlorophenyl)-N-methyl-amino]piperidin-1-yl}phenoxymethyl)-2-methyl-6-nitro-2,3-dihydroimidazo[2,1-b]oxazole (hereinafter referred to as "compound (C-RS)")

(R)-2-methyl-6-nitro-2-{4-[4-(4-trifluoromethoxybenzyl)piperidin-1-yl]phenoxymethyl}-2,3-dihydroimidazo[2,1-b]oxazole (hereinafter referred to as "compound (D-R)")

(S)-2-methyl-6-nitro-2-{4-[4-(4-trifluoromethoxybenzyl)piperidin-1-yl]phenoxymethyl}-2,3-dihydroimidazo[2,1-b]oxazole (hereinafter referred to as "compound (D-S)")

(RS)-2-methyl-6-nitro-2-{4-[4-(4-trifluoromethoxybenzyl)piperidin-1-yl]phenoxymethyl}-2,3-dihydroimidazo[2,1-b]oxazole (hereinafter referred to as "compound (D-RS)")

(R)-2-{4-[4-(3,4-dichlorobenzyl)piperidin-1-yl]phenoxymethyl}-2-methyl-6-nitro-2,3-dihydroimidazo[2,1-b]oxazole (hereinafter referred to as "compound (E-R)")

(S)-2-{4-[4-(3,4-dichlorobenzyl)piperidin-1-yl]phenoxymethyl}-2-methyl-6-nitro-2,3-dihydroimidazo[2,1-b]oxazole (hereinafter referred to (hereinafter referred to as "compound (G-RS)")

(R)-6-nitro-2-{4-[4-(4-trifluoromethoxybenzyloxy)piperidin-1-yl]phenoxymethyl}-2,3-dihydroimidazo[2,1-b]oxazole (hereinafter referred to as "compound (H-R)")

(S)-6-nitro-2-{4-[4-(4-trifluoromethoxybenzyloxy)piperidin-1-yl]phenoxymethyl}-2,3-dihydroimidazo[2,1-b]oxazole (hereinafter referred to as "compound (H-S)")

(RS)-6-nitro-2-{4-[4-(4-trifluoromethoxybenzyloxy)piperidin-1-yl]phenoxymethyl}-2,3-dihydroimidazo[2,1-b]oxazole (hereinafter referred to as "compound (H-RS)")

(R)-2-methyl-6-nitro-2-(4-{4-[2-(4-trifluoromethoxyphenyl)ethyl]piperidin-1-yl}phenoxymethyl)-2,3-dihydroimidazo[2,1-b]oxazole (hereinafter referred to as "compound (1-R)")

(S)-2-methyl-6-nitro-2-(4-{4-[2-(4-trifluoromethoxyphenyl)ethyl]piperidin-1-yl}phenoxymethyl)-2,3-dihydroimidazo[2,1-b]oxazole (hereinafter referred to as "compound (I-S)")

(RS)-2-methyl-6-nitro-2-(4-{4-[2-(4-trifluoromethoxyphenyl)ethyl]piperidin-1-yl}phenoxymethyl)-2,3-dihydroimidazo[2,1-b]oxazole (hereinafter referred to as "compound (I-RS)")

(R)-2-{4-[4-(4-chlorophenoxymethyl)piperidin-1-yl]phenoxymethyl}-2-methyl-6-nitro-2,3-dihydroimidazo[2,1-b]oxazole (hereinafter referred to as "compound (J-R)")

(S)-2-{4-[4-(4-chlorophenoxymethyl)piperidin-1-yl]phenoxymethyl}-2-methyl-6-nitro-2,3-dihydroimidazo[2,1-b]oxazole (hereinafter referred to as "compound (J-S)")

(RS)-2-{4-[4-(4-chlorophenoxymethyl)piperidin-1-yl]phenoxymethyl}-2-methyl-6-nitro-2,3-dihydroimidazo[2,1-b]oxazole (hereinafter referred to as "compound (J-RS)")

(R)-6-nitro-2-{4-[4-(4-trifluoromethoxyphenoxymethyl)piperidin-1-yl]phenoxymethyl}-2,3-dihydroimidazo[2,1-b]oxazole (hereinafter referred to as "compound (K-R)")

(S)-6-nitro-2-{4-[4-(4-trifluoromethoxyphenoxymethyl)piperidin-1-yl]phenoxymethyl}-2,3-dihydroimidazo[2,1-b]oxazole (hereinafter referred to as "compound (K-S)")

(RS)-6-nitro-2-{4-[4-(4-trifluoromethoxyphenoxymethyl)piperidin-1-yl]phenoxymethyl}-2,3-dihydroimidazo[2,1-b]oxazole (hereinafter referred to as "compound (K-RS)")

(R)-6-nitro-2-{4-[4-(4-trifluoromethoxybenzyl)piperidin-1-yl]phenoxymethyl}-2,3-dihydroimidazo[2,1-b]oxazole (hereinafter referred to as "compound (L-R)")

(S)-6-nitro-2-{4-[4-(4-trifluoromethoxybenzyl)piperidin-1-yl]phenoxymethyl}-2,3-dihydroimidazo[2,1-b]oxazole (hereinafter referred to as "compound (L-S)")

(RS)-6-nitro-2-{4-[4-(4-trifluoromethoxybenzyl)piperidin-1-yl]phenoxymethyl}-2,3-dihydroimidazo[2,1-b]oxazole (hereinafter referred to as "compound (L-RS)")

(R)-2-methyl-6-nitro-2-{4-[4-(4-trifluoromethoxybenzyloxy)piperidin-1-yl]phenoxymethyl}-2,3-dihydroimidazo[2,1-b]oxazole (hereinafter referred to as "compound (M-R)")

(S)-2-methyl-6-nitro-2-{4-[4-(4-trifluoromethoxybenzyloxy)piperidin-1-yl]phenoxymethyl}-2,3-dihydroimidazo[2,1-4]oxazole (hereinafter referred to as "compound (M-S)")

(RS)-2-methyl-6-nitro-2-{4-[4-(4-trifluoromethoxybenzyloxy)piperidin-1-yl]phenoxymethyl}-2,3-dihydroimidazo[2,1-b]oxazole (hereinafter referred to as "compound (M-RS)")

(R)-2-methyl-6-nitro-2-(4-{4-[3-(4-trifluoromethoxyphenyl)-2-propenyl]piperazin-1-yl}phenoxymethyl)-2,3-dihydroimidazo[2,1-b]oxazole (hereinafter referred to as "compound (N—R)")

(S)-2-methyl-6-nitro-2-(4-{4-[3-(4-trifluoromethoxyphenyl)-2-propenyl]piperazin-1-yl}phenoxymethyl)-2,3-dihydroimidazo[2,1-b]oxazole (hereinafter referred to as "compound (N—S)")

(RS)-2-methyl-6-nitro-2-(4-{4-[3-(4-trifluoromethoxyphenyl)-2-propenyl]piperazin-1-yl}phenoxymethyl)-2,3-dihydroimidazo[2,1-b]oxazole (hereinafter referred to as "compound (N—RS)")

(R)-2-{4-[4-(4-chlorophenoxymethyl)piperidin-1-yl]phenoxymethyl}-6-nitro-2,3-dihydroimidazo[2,1-b]oxazole (hereinafter referred to as "compound (O—R)")

(S)-2-{4-[4-(4-chlorophenoxymethyl)piperidin-1-yl]phenoxymethyl}-6-nitro-2,3-dihydroimidazo[2,1-b]oxazole (hereinafter referred to as "compound (O—S)")

(RS)-2-(4-[4-(4-chlorophenoxymethyl)piperidin-1-yl]phenoxymethyl]-6-nitro-2,3-dihydroimidazo[2,1-b]oxazole (hereinafter referred to as "compound (O—RS)")

(R)-6-nitro-2-{4-[4-(4-trifluoromethylphenoxymethyl)piperidin-1-yl]phenoxymethyl}-2,3-dihydroimidazo[2,1-b]oxazole (hereinafter referred to as "compound (P-R)")

(S)-6-nitro-2-{4-[4-(4-trifluoromethylphenoxymethyl)piperidin-1-yl]phenoxymethyl}-2,3-dihydroimidazo[2,1-b]oxazole (hereinafter referred to as "compound (P-S)")

(RS)-6-nitro-2-{4-[4-(4-trifluoromethylphenoxymethyl)piperidin-1-yl]phenoxymethyl}-2,3-dihydroimidazo[2,1-b]oxazole (hereinafter referred to as "compound (P-RS)")

(R)-2-methyl-6-nitro-2-{4-[4-(4-trifluoromethylphenoxymethyl)piperadin-1-yl]phenoxymethyl}-2,3-dihydroimidazo[2,1-b]oxazole (hereinafter referred to as "compound (Q-R)")

(S)-2-methyl-6-nitro-2-{4-[4-(4-trifluoromethylphenoxymethyl)piperidin-1-yl]phenoxymethyl}-2,3-dihydroimidazo[2,1-b]oxazole (hereinafter referred to as "compound (Q-S)")

(RS)-2-methyl-6-nitro-2-{4-[4-(4-trifluoromethylphenoxymethyl)piperidin-1-yl]phenoxymethyl}-2,3-dihydroimidazo[2,1-b]oxazole (hereinafter referred to as "compound (Q-RS)")

(R)-2-methyl-6-nitro-2-{4-[4-(4-trifluoromethoxyphenoxymethyl)piperidin-1-yl]phenoxymethyl}-2,3-dihydroimidazo[2,1-b]oxazole (hereinafter referred to as "compound (R—R)")

(S)-2-methyl-6-nitro-2-{4-[4-(4-trifluoromethoxyphenoxymethyl)piperidin-1-yl]phenoxymethyl}-2,3-dihydroimidazo[2,1-b]oxazole (hereinafter referred to as "compound (R—S)")

(RS)-2-methyl-6-nitro-2-{4-[4-(4-trifluoromethoxyphenoxymethyl)piperidin-1-yl]phenoxymethyl}-2,3-dihydroimidazo[2,1-b]oxazole (hereinafter referred to as "compound (R—RS)")

(R)-6-nitro-2-(4-{4-[3-(4-trifluoromethoxyphenyl)propyl]piperidin-1-yl}phenoxymethyl)-2,3-dihydroimidazo[2,1-b]oxazole (hereinafter referred to as "compound (S—R)")

(S)-6-nitro-2-(4-{4-[3-(4-trifluoromethoxyphenyl)propyl]piperidin-1-yl}phenoxymethyl)-2,3-dihydroimidazo[2,1-b]oxazole (hereinafter referred to as "compound (S—S)")

(RS)-6-nitro-2-(4-{4-[3-(4-trifluoromethoxyphenyl)propyl]piperidin-1-yl}phenoxymethyl)-2,3-dihydroimidazo[2,1-b]oxazole (hereinafter referred to as "compound (S—RS)")

(R)-5-(2-methyl-6-nitro-2,3-dihydroimidazo[2,1-b]oxazol-2-ylmethoxy)-2-[4-(4-trifluoromethoxybenzyl)piperidin-1-yl]-pyridine (hereinafter referred to as "compound (T-R)")

(S)-5-(2-methyl-6-nitro-2,3-dihydroimidazo[2,1-b]oxazol-2-ylmethoxy)-2-[4-(4-trifluoromethoxybenzyl)piperidin-1-yl]-pyridine (hereinafter referred to as "compound (T-S)")

(RS)-5-(2-methyl-6-nitro-2,3-dihydroimidazo[2,1-b]oxazol-2-ylmethoxy)-2-[4-(4-trifluoromethoxybenzyl)piperidin-1-yl]-pyridine (hereinafter referred to as "compound (T-RS)")

(R)-2'-methyl-6-nitro-2-{4-[4-(5-trifluoromethylbenzofuran-2-ylmethyl)piperidin-1-yl]phenoxymethyl}-2,3-dihydroimidazo[2,1-b]oxazole (hereinafter referred to as "compound (U-R)")

(S)-2-methyl-6-nitro-2-{4-[4-(5-trifluoromethylbenzofuran-2-ylmethyl)piperidin-1-yl]phenoxymethyl}-2,3-dlhydroLmidazo[2,1-b]oxazole (hereinafter referred to as "compound (U-S)")

(RS)-2-methyl-6-nitro-2-{4-[4-(5-trifluoromethylbenzofuran-2-ylmethyl)piperidin-1-yl]phenoxymethyl}-2,3-dihydroimidazo[2,1-b]oxazole (hereinafter referred to as "compound (U-RS)")

(R)-6-(2-methyl-6-nitro-2,3-dihydroimidazo[2,1-b]oxazol-2-ylmethoxy)-2-[4-(4-trifluoromethoxybenzyl)piperidin-1-yl]quinoline (hereinafter referred to as "compound (V-R)")

(S)-6-(2-methyl-6-nitro-2,3-dihydroimidazo[2,1-b]oxazol-2-ylmethoxy)-2-[4-(4-trifluoromethoxybenzyl)piperidin-1-yl]quinoline (hereinafter referred to as "compound (V-S)")

(RS)-6-(2-methyl-6-nitro-2,3-dihydroimidazo[2,1-b]oxazol-2-ylmethoxy)-2-[4-(4-trifluoromethoxybenzyl)piperidin-1-yl]quinoline (hereinafter referred to as "compound (V-RS)")

(R)-6-nitro-2-{4-[4-(4'-trifluoromethylbiphenyl-4-ylmethyl)piperazin-1-yl]phenoxymethyl}-2,3-dihydroimidazo[2,1-b]oxazole (hereinafter referred to as "compound (W—R)")

(S)-6-nitro-2-{4-[4-(4'-trifluoromethylbiphenyl-4-ylmethyl)piperazin-1-yl]phenoxymethyl}-2,3-dihydroimidazo[2,1-b]oxazole (hereinafter referred to as, "compound (W—S)")

(RS)-6-nitro-2-{4-[4-(4'-trifluoromethylbiphenyl-4-ylmethyl)piperazin-1-yl]phenoxymethyl}-2', 3-dihydroimidazo[2,1-b]oxazole (hereinafter referred to as "compound (W—RS)").

(R)-4-[(2-methyl-6-nitro-2,3-dihydroimidazo[2,1-b]oxazol-2-yl)methyl]-N-[(E)-4-trifluoromethylbenzylidene]piperazin-1-amine (hereinafter referred to as "compound (X—R)")

(S)-4-[(2-methyl-6-nitro-2,3-dihydroimidazo[2,1-b]oxazol-2-yl)methyl]-N-[(E)-4-trifluoromethylbenzylidene]piperazin-1-amine (hereinafter referred to as "compound (X—S)")

(RS)-4-[(2-methyl-6-nitro-2,3-dihydroimidazo[2,1-b]oxazol-2-yl)methyl]-N-[(E)-4-trifluoromethylbenzylidene]piperazin-1-amine (hereinafter referred to as "compound (X—RS)")

(R)-2-methyl-6-nitro-2-(4-{4-[(E)-3-(4-trifluoromethylphenyl)-2-propenyl]piperazin-1-yl}phenoxymethyl)-2,3-dihydroimidazo[2,1-b]oxazole (hereinafter referred to as "compound (Y—R)")

(S)-2-methyl-6-nitro-2-(4-{4-[(E)-3-(4-trifluoromethylphenyl)-2-propenyl]piperazin-1-yl}phenoxymethyl)-2,3-dihydroimidazo[2,1-b]oxazole (hereinafter referred to as "compound (Y—S)")

(RS)-2-methyl-6-nitro-2-(4-{4-[(E)-3-(4-trifluoromethylphenyl)-2-propenyl]piperazin-1-yl}phenoxymethyl)-2,3-dihydroimidazo[2,1-b]oxazole (hereinafter referred to as "compound (Y—RS)")

The present invention preferably uses at least one selected from the group consisting of the oxazole compounds described above, optically active forms thereof and pharmacologically acceptable salts thereof.

Optically active forms of oxazole compounds include R and S forms.

Pharmacologically acceptable salts include, for example, inorganic acid salts such as sulfate, nitrate, hydrochloride, phosphate and hydrobromide, sulfonic acid salts such as p-toluenesulfonate, methanesulfonate and ethanesulfonate, and organic acid salts such as oxalate, maleate, fumarate, malate, tartrate, citrate, succinate and benzoate.

The more preferred oxazole compounds (I) are at least one selected from the group consisting of compounds (A-R), compounds (Q-R), optically active forms thereof and pharmacologically acceptable salts thereof.

The above oxazole compounds, optically active forms thereof and pharmacologically acceptable salts thereof (I), their manufacturing method, doses in their use, etc. are disclosed in JP-A-2004-149527 and WO2005-042542, the disclosures of which are incorporated herein by reference as a part of the specification.

The drugs (II) which may be combined with oxazole compounds (I) in the present invention include, for example, drugs selected from the followings. One or more drugs (II) may be used in combination. It is preferred that one or more drugs selected from antituberculous drugs of the following (1) are used in combination.

(1) Primary Antituberculous Drugs

The primary antituberculous drugs include, for example, rifamycin and related anti-bacterial drugs (rifampicin, rifabutin, rifapentine, etc.), isoniazid, ethambutol, streptomycin, pyrazinamide, etc. These primary antituberculous drugs may be in the form of salts such as sodium methanesulfonate and hydrochloride. The specific examples include, for example, isoniazid sodium methanesulfonate, ethambutol hydrochloride, streptomycin sulfate, etc.

(2) Secondary Antituberculous Drugs

The secondary antituberculous drugs include, for example, p-aminosalicylic acid, alumino-p-aminosalicylic acid, ethionamide, prothionamide, enviomycin, kanamycin, capreomycin, cycloserine, thloacetazone, clofazimine, diaphenylsulfone, etc. These secondary antituberculous drugs may be in the form of salts such as calcium salt, sulfate, etc. The specific examples include, for example, calcium p-aminosalicylate, calcium alumino-p-aminosalicylate, enviomycin sulfate, kanamycin sulfate, etc.

(3) Quinolone Antibacterial Drugs

The quinolone antibacterial drugs include, for example, gatifloxacin, moxifloxacin, grepafloxacin, nadifloxacin, nalidixic acid, pipemidic acid, piromidic acid, enoxacin, norfloxacin, ofloxacin, tosufloxacin, clprofloxacin, lomefloxacin, sparfloxacin, fleroxacin, levofloxacin, prulifloxacin, pazufloxacin, linezolid, etc. These quinolone antibacterial drugs may be in the form of salts such as tosylate, hydrochloride and mesylate, and hydrates. The specific examples include, for example, tosufloxacin tosylate, ciprofloxacin hydrochloride, lomefloxacin hydrochloride, pazufloxacin mesylate, gatifloxacin hydrate, pipemidic acid trlhydrate, etc.

(4) Macrolide Antibacterial Drugs

The macrolide antibacterial drugs include, for example, clarithromycin, azithromycin, erythromycin, etc. These macrolide antibacterial drugs may be in the form of hydrates. The specific examples include, for example, azithromycin hydrate, etc.

(5) Sulfa Drugs

The sulfa drugs include, for example, sulfamethizole, sulfisoxazole, sulfamonomethoxine, sulfadimethoxine, sulfamethizole, salazosulfapyridine, sulfadiazine, etc. These sulfa drugs may be in the form of salts such as silver salt etc. The specific examples include, for example, sulfadiazine silver, etc.

(6) Anti-HIV Drugs

The anti-HIV drugs include, for example, (a) a reverse transcriptase inhibitor based on a nucleic acid [zidovudine, didanosine, zalcitabine, lamivudine, stavudine, abacavir, adefovir, adefovir dipivoxil, fozivudine tidoxil, etc.], (b) a reverse transcriptase inhibitor based on a non-nucleic acid [nevirapine, delavirdine, efavirenz, loviride, immunocal, oltipraz, etc.], (c) a protease inhibitor [saquinavir, ritonavir, indinavir, nelfinavir, amprenavir, palinavir, lasinavir, lopinavir, etc.], etc. These anti-HIV drugs may be in the form of salts.

The antituberculous therapeutic drugs of the present invention combined with the oxazole compounds (I) and the above drugs (II) include preferably the following (1) to (11):

(1) antituberculous therapeutic drugs comprising a combination of oxazole compounds (I) with at least one selected from the group consisting of the primary antituberculous drugs (preferably, rifamycin and related anti-bacterial drugs (preferably, at least one selected from the group consisting of rifampicin, rifabutin and rifapentine, and more preferably rifampicin), at least one selected from the group consisting of isoniazid, ethambutol, streptomycin, pyrazinamide and salts thereof) and the secondary antituberculous drugs (preferably, at least one selected from the group consisting of enviomycin, kanamycin, capreomycin, cycloserine, thioacetazone, clofazimine and salts thereof);

(2) antituberculous therapeutic drugs comprising a combination of oxazole compounds (I) with at least one primary antituberculous drug selected from the group consisting of rifamycin and related anti-bacterial drugs (preferably, at least one selected from the group consisting of rifampicin, rifabutin and rifapentine, and more preferably rifampicin), isoniazid, isoniazid sodium methahesulfonate, ethambutol hydrochloride, streptomycin, and pyrazinamide;

(3) antituberculous therapeutic drugs comprising a combination of oxazole compounds (I), (i) rifamycin and related anti-bacterial drugs (preferably, at least one selected from the group consisting of rifampicin, rifabutin and rifapentine, and more preferably rifampicin) with (ii) at least one primary antituberculous drug selected from the group consisting of isonlazid, ethambutol hydrochloride, streptomycin and pyrazinamide;

(4) antituberculous therapeutic drugs comprising a combination of oxazole compounds (I), (i) rifamycin and related anti-bacterial drugs (preferably, at least one selected from the group consisting of rifampicin, rifabutin and rifapentine, and more preferably rifampicin) with (ii) pyrazinamide;

(5) antituberculous therapeutic drugs comprising a combination of oxazole compounds (I) with at least one primary antituberculous drug selected from the group consisting of (i) rifamycin and related anti-bacterial drugs (preferably, at least one selected from the group consisting of rifampicin, rifabutin and rifapentine, and more preferably rifampicin), (ii) pyrazinamide and (iii) isoniazid, isoniazid sodium methanesulfonate, ethambutol hydrochloride, and streptomycin;

(6) antituberculous therapeutic drugs comprising a combination of oxazole compounds (I) with at least one quinolone antibacterial drug selected from the group consisting of gatifloxacin hydrate, moxifloxacin, and grepafloxacin;

(7) antituberculous therapeutic drugs comprising a combination of oxazole compounds (I), (A) at least one quinolone antibacterial drugs selected from the group consisting of gatifloxacin hydrate and moxifloxacin and (B) at least one primary antituberculous therapeutic drug selected from the group consisting of rifamycin and related antibacterial drugs (preferably, at least one selected from the group consisting of rifampicin, rifabutin and rifapentine, and more preferably rifampicin), isoniazid, isonlazid sodium methanesulfonate, ethambutol hydrochloride, streptomycin and pyrazinamide.

(8) antituberculous therapeutic drugs comprising a combination of oxazole compounds (I), (A) at least one quinolone antibacterial drug selected from the group consisting of gatifloxacin hydrate and moxifloxacin, (B-1) rifamycin and related antibacterial drugs (preferably, at least one selected from the group consisting of rifampicin, rifabutin and rifapentine, and more preferably rifampicin) and (B-ii) at least one primary antituberculous therapeutic drug selected from the group consisting of isonlazid, tethambutol hydrochloride, streptomycin and pyrazinamide.

(9) antituberculous theArapeutic drugs comprising a combination of oxazole compounds (I), (A) moxifloxacin, (B-i) rifanpicin and (B-ii) pyrazinamide.

(10) antituberculous therapeutic drugs comprising a combination of oxazole compounds (I) with at least one quinolone antibacterial drug selected from the group consisting of gatifloxacin hydrate and moxifloxacin;

(11) antituberculous therapeutic drugs comprising a combination of oxazole compounds (I) with at least one macrolide antibacterial drug selected from the group consisting of clarithromycin and azithromycin hydrate; and

(12) antituberculous therapeutic drugs comprising a combination of oxazole compounds (I) with anti-HIV drugs which are (a) a reverse transcriptase inhibitor based on a nucleic acid, (b) a reverse transcriptase inhibitor based on a non-nucleic acid or (c) a protease inhibitor.

The above oxazole compounds (I) and the above drugs (II) may be administered orally or parenterally.

wherein, when using a medicament comprising a combination of oxazole compounds (I) of the present invention and drugs (II) described above, administration period of oxazole compounds (I) of the present invention and drugs (II) described above is not limited, therefore, oxazole compounds (I) of the present invention or their pharmaceutical compositions and drugs (II) described above of their pharmaceutical compositions may be administered to the subject concomitantly or with time difference. When administering oxazole compounds (I) and drugs (II), while they may be administered concomitantly, drugs (II) may be administered earlier followed by administration of oxazole compounds (I) or oxazole compounds (I) may be administered earlier followed by administration of drugs (II). When administering with time difference, the time difference varies depending on active ingredients, formulations and methods of administration. When administering drugs (II) earlier, for example, the method includes administration of oxazole compounds (I) within 1 minute to 3 days, preferably within 10 minutes to 1 day, more preferably within 15 minutes to 1 hour after administration of drugs (II).

The dose of drugs (II) described above may conform the dose used clinically and may be appropriately selected depending on a subject to be administered, an administration route, a disease, a combination etc.

The administration form of drugs of the present invention used in combination is not particularly limited only if oxazole compounds (I) of the present invention are administered with drugs (II) described above. Such administration forms include, for example, (1) administration of single preparations obtained by formulating oxazole compounds (I) and drugs (II) described above simultaneously, (2) simultaneous administration in the same administration route of two preparations obtained by formulating oxazole compounds (I) and drugs (II) described above separately, (3) administration with time difference in the same administration route of two preparations obtained by formulating oxazole compounds (I) and drugs (II) described above separately (for example, administration in the order of oxazole compounds (I); one or more drugs (II) described above, or in the reversed order), (4) simultaneous administration in the different administration route of two preparations obtained by formulating oxazole compounds (I) and drugs (II) described above separately, (5) administration with time difference in the different administration route of one or more preparations obtained by formulating oxazole compounds (I) and drugs (II) described above separately (for example, administration in the order of oxazole compounds (I); one or more drugs (II) described above, or in the reversed order).

Further, when using a medicament of a single oxazole compound (I) or that comprising a combination of oxazole compounds (I) with drugs for concomitant use, administration is performed, for example, intermittently with interval periods set in order to relieve and eliminate side effects of the existing drugs for concomitant use being used in combination. When administering intermittently, while interval period of the present invention will vary corresponding to different situations and be determined as needed by the physician's judgment, oxazole compounds (I) are desirably administered at regular intervals.

Therefore, in an embodiment of the present invention, oxazole compounds (I) are administered at intervals of about 48 hours or more (preferably, about 72 hours or more, more preferably, about 7 days or more).

Further, in an embodiment of the present invention, oxazole compounds (I) are administered not more than 5 times, preferably not more than 3 times, preferably not more than 2 times, more preferably one time a week. The medication mode of 3 times a week includes such a procedure that medication is dosed continuously for 3 days from initiation of administration followed by other 4 days of interval in 7 days. The medication mode of 2 times a week includes such a procedure that medication is dosed continuously for 2 days from initiation of administration followed by other 5 days of interval in 7 days. Further, the treatment mode of 5 times a week includes such a procedure that medication is dosed continuously for 5 days per week followed by the other 2 days of interval.

Any of oxazole compounds (I) which are components of the present invention, drugs (II) and/or medicaments of the present invention comprising a combination of oxazole compounds (I) with drugs (II) have low toxicity, and oxazole compounds (I) and/or drugs (II) may be mixed with pharmacologically acceptable carriers according to known methods and administered safely as pharmaceutical compositions, for example, tablets (including sugar-coated and film-coated tablets), powders, granules, capsules (including soft capsules), solutions, injections, suppositories, sustained drugs orally or parenterally (for example, topically, rectally, intravenously etc.). Injections may be administered intravenously, intramuscularly, subcutaneously or intraorganly, or directly into the lesion. Pharmacologically acceptable carriers which may be used in production of drugs to be used concomitantly of the present invention include excipients, disintegrators, binders, glidants, lubricants, coating agents, coloring agents, suspending agents, sweeteners or surfactants, which are used as needed to make common forms of pharmaceutical preparations according to known methods. Forms of pharmaceutical preparations include, for example, powders, tablets, pills, capsules, etc.

The excipients include, for example, lactose, anhydrous lactose, sucrose, saccharose, D-mannitol, D-sorbitol, xylitol, erythritol, dextrin, crystalline cellulose, microcrystalline cellulose corn starch, potato starch, anhydrous calcium hyrogenphosphate, etc.

The disintegrators include, for example, sodium carboxymethylstarch, carmellose, carmellose calcium, carmellose sodium, croscarmellose sodium, crospovidone, low substituted hydroxypropylcellulose, partially pregelatinized starch, etc.

The binders include, for example, hydroxypropylcellulose, hydroxypropylmethylcellulose, polyvinylpyrrolidone, pregelatinized starch, syrup, starch syrup, etc.

The glidants include, for example, light anhydrous silicic acid, synthetic aluminum silicate, hydrous silicon dioxide, calcium stearate, metasilicate magnesium aluminate, talc, etc.

The lubricants include, for example, magnesium stearate, calcium stearate, magnesium silicate, magnesium oxide, talc, hydrogenated oil, sucrose fatty acid ester, sodium fumarate stearyl, etc.

The coating agents include, for example, hydroxypropylmethylcellulose, polyvinyl alcohol, polysorbate, macrogol, talc, etc.

The coloring agents include, for example, yellow iron sesquioxide, brown iron oxide, iron sesquloxide, titanium oxide, Food Blue No. 1, Food Red No. 2, Food Red No. 3, Food Yellow No. 4, etc.

The suspending agents include, for example, polysorbate, polyethyleneglycol, acacia gum, glycerin, gelatin, etc.

The sweeteners include, for example, aspartame, saccharin, sodium saccharin, starch syrup, fructose, etc.

The surfactants include, for example, sodium laurate, polysorbate, polyoxyethylene hydrogenated castor oil, etc.

Capsules are prepared by packing into hard capsules including gelatin capsules, hydroxypropylmethylcellulose capsules and polyvinylalcohol capsules as well as gelatin soft capsules according to known methods. Pharmaceutical materials include conventional different organic and inorganic carrier substances, for example, excipients, lubricants, binders and disintegrators in solid preparations, or dispersants, solubilizers, suspending agents, agents for isotonicity, buffering agents and agents for analgesia in liquid preparations. In addition, additives including common preservatives, antioxidants, coloring agents, sweeteners, adsorbents, wetting agents may be used in appropriate amount as needed.

In the present invention, using ratio of oxazole compounds (I) and drugs (II) described above may be usually about 0.01-100 parts by weight of the latter based on 1 part by weight of the former, preferably about 0.1-60 parts by weight, more preferably about 1-60 parts by weight.

Further, in the case where drugs (II) described above comprise in combination (i) rifampicin with (ii) at least one antituberculous drug selected from the group consisting of isonlazid, ethambutol hydrochloride, streptomycin and pyrazinamide, using ratio of (i) rifampicin and the antituberculous drug of (ii) may be about 0.1-10 parts by weight of the latter based on 1 part by weight of the former, preferably about 0.3-2.5 parts by weight.

Further, in the case where drugs (II) described above comprise in combination (i) rifampicin, (ii) pyrazinamide and (iii) at least one antituberculous drug selected from the group consisting of isoniazid, ethambutol and streptomycin, using ratio of (i) rifampicin and (ii) pyrazinamide may be usually about 1-10 parts by weight of the latter based on 1 part by the weight of the former, preferably about 1.5-4 parts by weight, and using ratio of (i) rifampicin and antituberculous drugs of (iii) may be usually about 0.1-10 parts by weight of the latter based on 1 part by weight of the former, preferably about 0.1-5 parts by weight, more preferably about 0.3-3 parts by weight.

Combining ratio of oxazole compounds (I) to drugs (II) in the antituberculous therapeutic drugs of the present invention may be selected appropriately depending on a subject to be administered, administration route, disease etc. For example, while total ratio of oxazole compounds (I) and drugs (II) in the antituberculous therapeutic dregs of the present invention differs depending on the form of preparations, it is usually in the range of about 0.01-99.99% by weight, preferably about 0.1-99.9% by weight, more preferably about 1-30% by weight based on the total preparation. In the residual part, pharmacologically acceptable carriers described above are used.

Additionally, in the cases where oxazole compounds (I) and drugs (II) are formulated separately, the contents may be similar.

While the dosage of the antituberculous therapeutic drugs of the present invention will vary depending on the type of oxazole compounds (I), age, weight, symptom, dosage form, administration method, administration period etc., usually, for example, about 0.01-about 1000 mg/kg, preferably about 0.01-about 100 mg/kg, more preferably about 0.1-about 100 mg/kg, especially about 0.1-about 50 mg/kg, most especially about 1.5-about 30 mg/kg a day per patient (adult, about 60 kg of weight) as oxazole compounds (I) and drugs (II) are administered intravenously from once to several times in divided amounts a day. Dosage will, of course, vary depending on different conditions as described above, the amounts less than the above described dose may be adequate or those exceeding the limit may be required. For drugs (II), it is possible to set any amount within the range where side effects are nonproblematic. While daily dosage with respect to drugs (II) will vary depending on degree of symptoms, age of the subject to be administered, sex, weight, difference of sensitivity, period of administration, interval, property of the pharmaceutical preparations, dispensing, type, type of active ingredients etc., it is administered as the amount of the drug, usually in the range of, but not particularly limited to, about 0.001-2000 mg per kg weight of a mammal, for example, orally, preferably about 0.01-500 mg, more preferably about 0.1-100 mg, 1-4 times a day in divided amounts.

Therefore, the present invention provides the kit for treatment of tuberculosis comprising a medicament containing oxazole compounds (I) described above as active ingredients and one or more drugs (II) selected from the group consisting of antituberculous drugs, quinolone antibacterial drugs, macrolide antibacterial drugs and anti-HIV drugs, and used to administer them at intervals of 48 hours or more.

Dosage forms of the medicament containing oxazole compounds (I) as active ingredients and drugs (II), carriers used in them, ratio of each ingredient, interval of administration may be used similarly as described above.

Preferred drugs (II) include, for example, primary antituberculous drugs, secondary antituberculous drugs and quinolone antibacterial drugs quinolone antibacterial drugs described above. Herein, preferred primary antituberculous drugs include at least one selected from the group consisting of isoniazid, isonlazid sodium methanesulfonate, pyrazinamide, rifampicin, streptomycin, streptomycin sulfate, ethambutol and ethambutol hydrochloride, more preferably at least one selected from the group consisting of rifampicin, pyrazinamide, isoniazid, ethambutol and streptomycin. Preferred secondary antituberculous drugs include at least one selected from the group consisting of enviomycin, enviomycin sulfate, kanamycin, kanamycin sulfate, capreomycin, cycloserine, thioacetazone and clofazimine. Preferred quinolone antibacterial drugs include at least one selected from the group consisting of gatifloxacin hydrate and moxifloxacin.

In the present invention, a combination of oxazole compounds (I) with drugs (II) which are antituberculous drugs used concomitantly having a different action mechanism exerts effects shown below compared with those in the case where oxazole compounds (I) or antituberculous drugs for concomitant use are administered singly.

(1) Oral administration is possible and the dosage can be reduced.

(2) A shorter treatment period can be set i.e. a short-term chemotherapy becomes possible.

(3) Side effects can be reduced.

(4) Sustained therapeutic effect can be attained.

(5) Synergistic effects can be obtained.

(6) Antituberculous dregs for concomitant use to be used in combination with oxazole compounds (I) can be selected corresponding to symptoms in patients (mild, severe or other)

(7) It is active against *Mycobacterium tuberculosis*, multidrug-resistant *Mycobacterium tuberculosis* and atypical acid-fast bacteria.

(8) Efficacy is shown against *Mycobacterium tuberculosis* infecting latently (latent *Mycobacterium tuberculosis*).

Such superior effects can be obtained. Further, by using a medicament of single oxazole compounds (I) or that comprising a combination of oxazole compounds (I) with drugs for concomitant use, it is possible, for example, to administer the above described drugs for concomitant use intermittently setting interval period of at least about 48 hours in order to relieve or eliminate side effects of existing antituberculous drugs being used in combination.

The following examples illustrate more clearly the present invention in detail.

EXAMPLE 1

In Vitro Experiment on the Combined Effect of an Oxazole Compound (I) and Another Agent The synergistic effect of an oxazole compound (I) and a known antituberculous drug, rifampicin (RFP) or ethambutol (EB) on a clinical isolate of tubercle bacillus was examined. Specifically, each 7H11 agar plate containing the compound (A-R) at a final concentration of 0.1-0.0002 µg/ml (a 2-fold dilution series), each agar plate of the same agar containing rifampicin at a final concentration of 1.56-0.0015 µg/ml, and each agar plate containing both drugs at each set of concentrations were prepared. A suspension of tubercle bacillus was prepared at about $10^6$ CFU/ml (for clinical isolates of tubercle bacillus, TBT-9 and TBT-14). About 10 µl aliquots thereof were inoculated on respective plates by using a multipoint inoculator. The plates were incubated at 37° C. for 2 weeks to determine minimum inhibitory concentrations (MIC) for cell growth. A similar test was performed by using ethambutol at concentrations of 12.5-0.024 µg/ml, and MIC was determined for each set of concentrations. From these results, an FIC Index ((MIC for a combination of compound (A-R) plus RFP or EB)/(MIC of compound (A-R) alone)+(MIC for a combination of RFP or EB plus the compound (A-R))/(MIC of RFP or EB alone)) was calculated for the set of concentrations with the least MIC. Results are shown in Table 1.

When compound (A-R) and rifampicin or ethambutol were combined with each other, FIC Index indicated 0.375 in both cases, as a result, a strong synergistic effect was demonstrated in a combination of both agents.

TABLE 1

Minimum inhibitory concentration (MIC) against tubercle bacillus

|  | FIC index | Compound (A-R) |  |
|---|---|---|---|
|  |  |  | RFP |
| Compound (A-R) & RFP | 0.375 | 0.006 (0.024) | 0.05 (0.39) |
|  |  |  | EB |
| Compound (A-R) & EB | 0.375 | 0.003 (0.012) | 0.2 (1.56) |

Unit: µg/ml
Numerical values in the Table: MIC in combination (MIC in alone)
FIC index: Synergistic effect; ≦0.5

EXAMPLE 2-1

In Vivo Experiments on the Combined Effect of the Oxazole Compound (I) and Other Agents
Therapeutic Effect in Combinations of Multiple Agents Tubercle bacillus, Kurono strain with 455 CFU was inoculated transtracheally in ICR mice and allowed to leave for 4 weeks to prepare an experimental mouse model of chronic tuberculosis. A combination of 2.5 mg/kg of the compound (A-R) (in FIG. 1-1, indicated as "O") with 5 mg/kg of rifampicin (in FIG. 1-1, indicated as "R") and 100 mg/kg of pyrazinamide (in FIG. 1-1, indicated as "Z") was given to this model. The dosing was conducted once a day for 56 days and the results were compared with those from a conventional regimen used for treatment of tuberculosis. The conventional regimen was dosing of rifampicin, isoniazid (in FIG. 1-1, indicated as "H"), ethambutol (in FIG. 1-1, indicated as "E") and pyrazinamide, 5 mg/kg, 10 mg/kg, 100 mg/kg and 100 mg/kg, respectively, once a day 56 days to the model mice hereinabove. To confirm decreasing viable cell counts of pulmonary tubercle-bacillus with time, the mice were euthanized by venesection from the inferior vena cava under anesthesia on the next day after dosing for 28 days (4 W) and 56 days (8W), and the lungs were extirpated aseptically. The extirpated lung in 2 ml of sterilized water was ground homogeneously with a glass homogenizer and diluted stepwise. Then, 0.1 ml of each diluted sample was smeared on the 7H11 agar plate medium and incubated until colonies appeared to calculate viable cell counts in the lung after the treatment.

As shown in FIG. 1-1, the triple therapy containing the compound (A-R) (in FIG. 1-1, indicated as "ORZ") was confirmed to show a stronger effect in spite of a smaller number of combined drugs than the known quadruple therapy regimen (in FIG. 1-1, indicated as "RHEZ"). Further, since the viable cell count of tubercle bacillus decreased in the early stage, the chemotherapy could be expected to be effective in a shorter time than that of the conventional antituberculous drugs.

EXAMPLE 2-2

In Vivo Experiments on the Combined Effect of the Oxazole Compound (1) and Other Agents
Therapeutic Effect in Combinations of Multiple Agents (2)

Tubercle bacillus, H37Rv strain with 2750 CFU was inoculated in ICR mice and allowed to leave for 4 weeks to prepare an experimental mouse model of chronic tuberculosis. Three drug combinations "ORZ", "OREZ" and "ORZM" selected from 2.5 mg/kg of the compound (A-R) (in FIG. 1-2, indicated as "O"), 10 mg/kg of rifampicin (in FIG. 1-2, indicated as "R"), 150 mg/kg of pyrazinamide (in FIG. 1-2, indicated as "Z"), 100 mg/kg of ethambutol (in FIG. 1-2, indicated as "E") and 100 mg/kg of moxifloxacin (in FIG. 1-2, indicated as "M") were given to this model. The dosing was conducted once a day for 56 days and the results were compared with those from a conventional regimen used for treatment of tuberculosis. The conventional regimen was dosing of rifampicin, isoniazid (in FIG. 1-1, indicated as "H"), ethambutol and pyrazinamide, 10 mg/kg, 25 mg/kg, 100 mg/kg and 150 mg/kg, respectively, once a day for 56 days to the model mice hereinabove. To confirm decreasing viable cell counts of pulmonary tubercle bacillus with time, the mice were euthanized by venesection from the inferior vena cava under anesthesia on the next day after dosing for and 56 days (8W), and the lungs were extirpated aseptically. The extirpated lung in 2 ml of sterilized water was ground homogeneously with a glass homogenizer and diluted stepwise. Then, 0.1 ml of each diluted sample was smeared on the 7H11 agar plate medium and incubated until colonies appeared to calculate viable cell counts in the lung after the treatment.

Figures 1, 2:
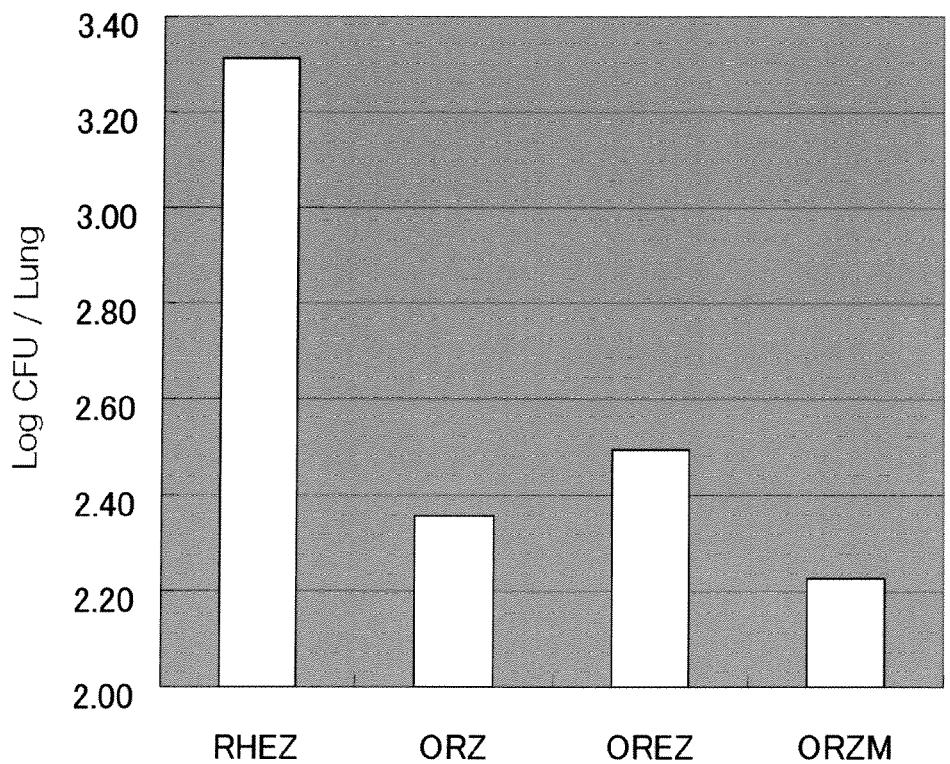
Figure 2:
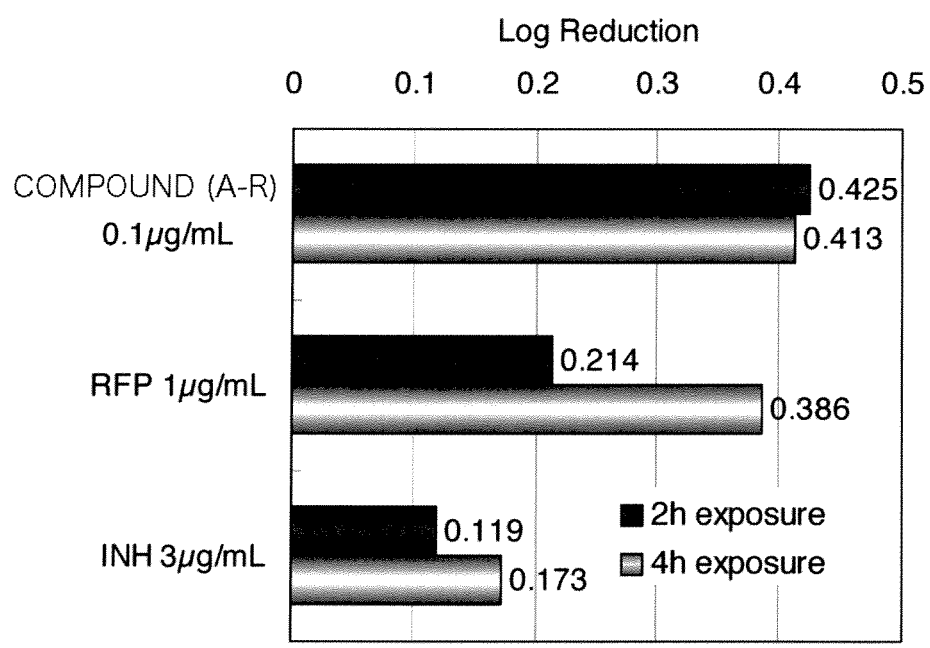

As shown in FIG. 1-2, all combination groups containing the compound (A-R) (in FIG. 1-2, indicated as "ORZ", "OREZ" and "ORZM") was confirmed to show a stronger effect in spite of a smaller number of combined drugs than the known quadruple therapy regimen (in FIG. 1-2, indicated as "RHEZ"). Further, since the viable cell count of tubercle bacillus decreased in the early stage, the chemotherapy could be expected to be effective in a shorter time than that of the conventional antituberculous drugs.

EXAMPLE 3

Evaluation of the Effect of the Oxazole Compound (I) on Intracellular Parasitic Tubercle Bacillus Evaluation of the effect of the oxazole compound (I) on intracellular parasitic tubercle bacillus was performed below.

3-1. Infection of Tubercle Bacillus in THP-1

A suspension of THP-1 cells with a cell density adjusted to $10^6$ cells/0.9 ml of RPMI1640-10% FBS medium (hereinafter abbreviated as RPMI1640 medium) was added in each well of a 24-well cell culture plate. A solution of phorbol 12-myristate 13-acetate (PMA) (0.1 ml) was added into the well containing added cells to the final concentration of 100 ng/ml. The plate was incubated at 37° C. for 48 hours under 5% $CO_2$ atmosphere to differentiate THP-1 cells into macrophage-like cells. The differentiated THP-1 cells were washed once with RPMI1640 medium to remove PMA solution. After replacing the medium in each well with fresh RPMI1640 medium 0.9 ml, prepared microbial suspension (*M. tuberculosis* H37Rv) 0.1 ml was added into each well. The plate was incubated at 37° C. for 4 hours under 5% $CO_2$ atmosphere to infect the bacteria into cells. Each well was washed twice with RPMI1640 medium for removing uninfected bacteria remaining in RPMI1640 medium. Further, RPMI1640 medium containing streptomycin (hereinafter designates as SM) 20 µg/ml was added and incubated for 20 hours in order to remove remaining external bacteria. After incubation, each well of the plate was washed twice with RPMI1640 medium to remove SM. After removing the washing medium from each well, it was replaced by fresh RPMI1640 medium 0.99 ml, at which time point was set as time 0 hour. For counting intracellular viable count before addition of test substance, the objective well in the plate was washed three times with phosphate buffer saline (PBS). After removing the final PBS washing solution, 0.1% SDS solution 0.5 ml was added into each well and allowed to stand at room temperature for 10 minutes or more to decompose cells. After neutralizing SDS by adding and mixing RPMI1640 medium 0.5 ml to each well, cell lysate was collected in test tubes. Ten-fold dilution series of the collected cell lysate with addition of distilled water were prepared, and each dilution solution 0.1 ml was smeared on 7H11 agar plate to prepare 3 plates, which were smeared with the collected cell lysate with bacteria having different dilution series. The smeared plates were sealed with vinyl tape to avoid drying and further incubated at 37° C. for 2-3 weeks. Number of appeared colonies was counted to calculate intracellular viable bacterial counts at time 0 hour according to judgment criterion.

3-2. Addition of Test Substance

Diluted solution of test substance 0.01 ml was added to each well of 24 well plate containing infected cells. The plate added with test substance was incubated at 37° C. under 5% $CO_2$ atmosphere, and after affecting for 2 or 4 hours by adding test substance, each well was washed three times with RPMI1640 medium for removal of the test substance. After removal of the test substance, fresh RPMI1640 medium 1 ml was added to each well and continued incubation.

3-3. Recovery, Dilution and Smearing on 7H11 Agar Plate of Intracellular Bacteria Intracellular bacteria were collected from plates incubated for 3 days (72 hours) after adding test substance by the following procedures. Specifically, each well in the plate was washed three times with PBS. After removing the final PBS washing solution, 0.1% SDS solution 0.5 ml was added into each well and allowed to stand at room temperature for 10 minutes or more to decompose cells. SDS solution was neutralized by adding RPMI1640 medium 0.5 ml to each well, and cell lysate, total volume of 1 ml, was collected in test tubes. Ten-fold dilution series of the collected cell lysate were prepared by using distilled water. Each diluted solution 0.1 ml was smeared on 7H11 agar plate to prepare 3 plates, which were smeared with the collected cell lysate with bacteria having different dilution series. The smeared plates were sealed with vinyl tape to avoid drying and further incubated at 37° C. for 2-3 weeks to count numbers of appeared colonies.

Log reduction of bacterial counts compared with the bacterial counts at time 0 hour before addition of test substance was shown based on experimental results (FIG. 2). As a result, in the group adding compound (A-R), stronger effect against intracellular parasitic tubercle bacillus was confirmed than in the group adding other antituberculous drugs. Although RFP showed the strongest effect in the conventional drugs, the compound (A-R) was found to exhibit the equivalent effect of the maximum concentration 3 µg/ml of RFP, even at the lowest test dose of the compound (A-R) 0.1 µg/ml in concentration employed in the study. In addition, strong effect was confirmed even in short term action for 2 hours, and this result suggests that the compound (A-R) has strong post antibiotic effect (PAE) against tubercle bacilli. Consequently, it is conceivable that the compound (A-R) can be a drug having sufficient effect even in the intermittent administration in the clinical field.

EXAMPLE 4

Evaluation of Drug Interaction Between Oxazole Compound (I) and Other Drugs

Since there are many cases in metabolism related drug interaction involved in cytochrome P450 (CYP) enzyme, elucidation of CYP molecular species involved in metabolism of antituberculous drug oxazole compound (I) is essential for safety use of the above described drug. In addition, since there is a possibility to occur drug interaction on the condition that multiple a combination of antituberculous drugs is conventionally applied, inhibitory action of oxazole compound (I) against each CYP enzyme is important to study. Various CYP enzymes are confirmed in the hepatic microsomal enzyme, and drug metabolism using the hepatic microsomal enzyme and inhibitory action of drug against each CYP enzyme can be tested in vitro. Therefore, in vitro metabolism of oxazole compound (I) using hepatic microsomal enzyme of human and various animals (mouse, rat, dog, rabbit and monkey), and in vitro inhibitory action of oxazole compound (I) against each CYP enzyme using human hepatic microsomal enzyme were examined.

4-1. In Vitro Metabolism of Oxazole Compound (I)

Studies on in vitro metabolism of oxazole compound (I) (compound (A-R)) were performed using hepatic microsomal enzyme of human and various animals (mouse, rat, dog, rabbit and monkey). Human microsome was obtained from Attached Primate Research Institute, HAB Discussion Group (Chiba, Japan). Reaction composition (0.5 ml) was consisting of 100 mM phosphate buffer (pH 7.4), 100 µM compound (A-R), 2.5 mM β-NADPH, 2.5 mM β-NADH and microsome protein 1 mg/ml, and the reaction was performed at 37° C. for 2 hours. The reaction was terminated by adding organic solvent (acetonitrile or ethyl acetate) and generated metabolites were extracted. The extracted metabolites were detected by using high performance liquid chromatography and liquid chromatograph electrospray ionization tandem mass spectrometry to confirm amount of generation.

As a result of in vitro metabolism of the compound (A-R) using hepatic microsomal enzyme of human and various animals (mouse, rat, dog, rabbit and monkey), almost no generated metabolites were confirmed. Consequently, the compound (A-R) might not be metabolized by an action of CYP enzyme.

4-2. Effect of the Oxazole Compound (I) on the Enzymatic Activity of Each Molecular Species of Cytochrome P450 (CYP)

Inhibitory action of the oxazole compound (I) (compound (A-R): 1-100 μM) on each molecular species of CYP in human hepatic microsome was assayed by measuring ethoxyresorufin deethylation activity (CYP1A1/2), coumarin The results of the above experiments indicated that the compound (A-R) did not exhibit inhibitory action and stimulation action against each CYP enzyme (CYP1A/2, CYP2A6, CYP2B6, CYP2C8/9, CYP2C19, CYP2D6, CYP2E1 and CYP3A4) activity up to 100 μM (Table 2). Table 2 shows the effect of the oxazole compound (I) on the enzymatic activity of each molecular species of cytochrome P450 (CYP).

TABLE 2

Effect of compound (A-R) on metabolic activiy of CYP1A1/2, CYP2A6, CYP2B6, CYP2C8/9, CYP2C19, CYP2D6, CYP2E1 and CYP3A4 in human hepatic microsome

| CYP | Enzyme reaction | Compound (A-R) or inhibitor | Relative activity (%) for control activity Concentration (μM) | | | | | |
|---|---|---|---|---|---|---|---|---|
| | | | 1 | 3 | 10 | 30 | 100 | 1000 |
| CYP1A1/2 | ethoxyresorufin deethylation activity | Compound (A-R) furafylline 7,8-benzoflavone | 99.8 | 101.4 | 98.4 | 102.5 | 98.6 32.3 3.8 | |
| CYP2A6 | coumarin hydroxylation activiy | Compound (A-R) diethyldithiocarbamine | 103.3 | 102.4 | 103.1 | 97.8 | 100.8 38.2 | |
| CYP2B6 | 7-benzyloxyresorufin debenzylation activity | Compound (A-R) orphenadrine | 110.6 | 108.9 | 118.3 | 112.8 | 122.3 118.8 | 72.0 |
| CYP2C8/9 | tolbutamide hydroxylation activity | Compound (A-R) sulfaphenazole quercetin | 106.8 | 111.4 | 107.2 | 107.8 | 108.5 25.5 30.6 | |
| CYP2C19 | S-mephenytoin hydroxylation activity | Compound (A-R) tranylcypromine | 115.6 | 109.0 | 113.3 | 106.5 | 107.6 16.6 | |
| CYP2D6 | bufuralol hydroxylation activity | Compound (A-R) quinidine | 102.2 | 102.4 | 99.1 | 103.3 | 97.8 0.0 | |
| CYP2E1 | chlorozoxazone hydroxylation activity | Compound (A-R) diethyldithiocarbamine | 107.8 | 110.3 | 110.8 | 112.4 | 112.5 55.0 | |
| CYP3A4 | testosterone 6β-hydroxylation activity | Compound (A-R) ketoconazole | 110.8 | 110.7 | 117.7 | 117.7 | 115.6 0.5 | |
| CYP3A4 | nifedipine oxidation activity | Compound (A-R) ketoconazole | 100.4 | 102.8 | 101.3 | 99.9 | 100.3 3.4 | |

Each substrate and concentration 7-ethoxyresorufin (0.5 μM), coumarin (2 μM), 7-benzyloxyresorufin (1.5 μM), tolbutamide (400 μM), S-mephenytoin (100 μM), bufuralol (20 μM), chlorozoxazone (100 μM), testosterone (100 μM) and nifedipine (50 μM)
Specifictivity of control for CYP1A1/2, CYP2A6, CYP2B6, CYP2C8/9, CYP2C19, CYP2D6, CYP2E1 and CYP3A4 (testosterone 6β-hydroxylation activity) and CYP3A4 (nifedipine oxidation activity) were 9.094, 142.3, 1.595, 32.75, 7.331, 14.43, 81.49, 840.9 and 1127 pmol/min/mg
Analyses of enzyme reaction and metabolites were performed with n = 2
Each data was expressed by means value hydroxylation activity (CYP2A6), 7-benzyloxyresorufin debenzylation activity (CYP2B6), tolbutamide hydroxylation activity (CYP2C8/9), S-mephenyloin hydroxylation activity (CYP2C19), bufuralol hydroxylation activity (CYP2D6), chlorzoxazone hydroxylation activity (CYP2E1), testosterone 6β-hydroxylation activity (CYP3A4) and nifedipine oxidation activity (CYP3A4).

Basic reaction composition (0.5 ml) was consisting of microsome protein 0.2-1 mg/ml, 100 mM phosphate buffer (pH 7.4), 0.1 mM EDTA, NADPH generation system (2.5 mM β-NADP, 25 mM glucose-6-phosphate, 2 units glucose-6-phosphate dehydrogenase and 10 mM magnesium chloride), with or without each substrate and inhibitor, and the reaction was performed at 37° C. for 10-60 minutes. Each substrate and its concentration used were 7-ethoxyresorufin (0.5 μM), coumarin (2 μM), 7-benzyloxyresorufin (1.5 μM), tolbutamide (400 μM), S-mephenyloin (100 μM), bufuralol (20 μM), chlorozoxazone (100 μM), testosterone (100 μM) and nifedipine (50 μM). 7,8-benzoflavone (1A1), furafylline (1A2), orphenadrine (2B6), quercetin (2C8), sulfaphenazole (2C9), tranylcypromine (2C19), quinidine (2D6), diethyldithiocarbamine (2A6 and 2E1) and ketoconazole (3A4) were used as specific inhibitors for each CYP activity.

Generated products after the metabolic response were measured by using high performance liquid chromatography after extraction.

Considering the above data, when oxazole compound (I) and other drug, which is metabolized mainly by CYP, are used in combination at the concentration of oxazole compound in clinical use, in which effect can be expected, there may be a little possibility to inhibit metabolic activity of the combined drug (II) by an action of oxazole compound (I) and to increase blood level of the combined drug (II), namely causing drug interaction.

EXAMPLE 5

In Vivo Experiments for Intermittent Administration

Experimental mouse tuberculosis model was prepared and treated by once a day administration of the compound (A-R) alone or for a combination of other conventional drugs. Maintaining an index of the therapeutic effect equivalent to such the effect, the compound (A-R) alone or for a combination of other conventional antituberculous drugs was administered, for example, three times a week, twice a week or once a week in order to obtain the same effect as above. The equivalent effect was confirmed to be exhibited and the compound (A-R) was confirmed to be available used for intermittent administration in vivo.

The invention claimed is:
1. An antituberculous therapeutic drug comprising:
(I) a compound selected from (R)-2-methyl-6-nitro-2-{4-[4-(4-trifluoromethoxyphenoxy)piperidin-1-yl]phenoxymethyl}-2,3-dihydroimidazo[2,1-b] oxazole and pharmacologically acceptable salts thereof, and
(II) at least one primary antituberculous drug, wherein the primary antituberculous drug comprises in combination (i) a compound selected from rifampicin and salts thereof, and (ii) at least one compound selected from the group of isoniazid, ethambutol, streptomycin, pyrazinamide and salts thereof.

2. The antituberculous therapeutic drug according to claim 1, wherein the primary antituberculous drug comprises in combination (i) a compound selected from rifampicin and salts thereof, and (ii) a compound selected from pyrazinamide and salts thereof.

3. The antituberculous therapeutic drug according to claim 2, wherein the primary antituberculous drug comprises in combination (i) a compound selected from rifampicin and salts thereof, (ii) a compound selected from pyrazinamide and salts thereof, and (iii) a compound selected from ethambutol and salts thereof.

* * * * *